United States Patent
Everhart et al.

(10) Patent No.: US 6,180,288 B1
(45) Date of Patent: *Jan. 30, 2001

(54) GEL SENSORS AND METHOD OF USE THEREOF

(75) Inventors: Dennis S. Everhart, Alpharetta; Rosann M. Kaylor, Cumming; Mark L. Jones, Atlanta, all of GA (US)

(73) Assignee: Kimberly-Clark Worldwide, Inc., Neenah, WI (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/821,464

(22) Filed: Mar. 21, 1997

(51) Int. Cl.$^7$ .................................................. G03F 7/16
(52) U.S. Cl. ........................ 430/2; 430/321; 430/320; 430/1; 422/82.06; 264/1.1; 436/531
(58) Field of Search .................................. 430/320, 321, 430/2, 1; 264/1.1; 422/82.05, 82.03, 82.04, 82.06; 436/529, 531

(56) References Cited

U.S. PATENT DOCUMENTS

| | | |
|---|---|---|
| 4,312,228 | 1/1982 | Wohltjen .................................. 73/23 |
| 4,363,874 | 12/1982 | Greenquist ................................ 435/7 |

(List continued on next page.)

FOREIGN PATENT DOCUMENTS

| | | |
|---|---|---|
| 0 453 820 | 10/1991 | (EP) . |
| 0 596 421 A1 | 5/1994 | (EP) . |
| 0 657 737 | 6/1995 | (EP) . |
| 2273772 | 6/1994 | (GB) . |
| WO 90/05305 | 5/1990 | (WO) . |
| 91/05999 | 5/1991 | (WO) . |
| 96/26435 | 8/1996 | (WO) . |
| WO 96/29629 | 9/1996 | (WO) . |
| 96/33971 | 10/1996 | (WO) . |
| 98/10334 | 3/1998 | (WO) . |

OTHER PUBLICATIONS

Erbach, R. et al. "Application of rod–like polymers . . . ", Sensors and Actuators B, 6, pp. 211–216, 1992.*

Kelkar et al., "Acoustic Plate Waves for Measurement of Electrical Properties of Liquids", Microchem. Journal, vol. 43, pp. 155–164 (1991).

Liedberg et al, "Molecular Gradients of ω–Substituted Alkanethiols on Gold: Preparation and Characterization", Langmuir, vol. 11, pp. 3821–3827 (1995).

Shana et al, "Analysis of electrical equivalent circuit of quartz crystal resonator loaded with viscous conductive liquids", Journal of Electroanalytical Chemistry, vol. 379, pp. 21–33 (1994).

Shana et al., "Quartz Crystal Resonators as Sensors in Liquids Using the Acoustoelectric Effect", Anal. Chem., vol. 66, pp. 1955–1964 (1994).

Kumar et al., "Features of gold having micrometer to centimeter dimensions can be formed through a combination of stamping with an elastomeric stamp and an alkanethiol "ink" following by chemical etching", Appl. Phys. Lett., vol. 63, pp. 2002–2004 (1993).

(List continued on next page.)

*Primary Examiner*—Martin Angebranndt
(74) *Attorney, Agent, or Firm*—Jones & Askew, LLP

(57) ABSTRACT

The present invention comprises an optically diffracting sensing device whose diffraction pattern changes upon exposure to some stimuli. The diffraction pattern may be two or three dimensional, and in one embodiment the change in diffraction patterns is recognizable to the untrained eye. The device comprises one or more gels coated onto patterned, self-assembling monolayers of alkanethiolates, carboxylic acids, hydroxamic acids, and phosphonic acids printed onto a variety of substrates, including glass, silicon, aluminum oxide, and thermoplastic films metallized with gold, or with an alloy such as nickel/gold. The present invention also comprises the method of making this device, and the use of this device.

36 Claims, 19 Drawing Sheets

U.S. PATENT DOCUMENTS

| | | | |
|---|---|---|---|
| 4,399,686 | 8/1983 | Kindlund et al. ......................... | 73/23 |
| 4,416,505 | 11/1983 | Dickson ................................... | 359/3 |
| 4,534,356 | 8/1985 | Papadakis ............................. | 128/635 |
| 4,561,286 | 12/1985 | Sekler et al. ............................ | 73/23 |
| 4,562,157 | 12/1985 | Lowe et al. ......................... | 435/291 |
| 4,596,697 | 6/1986 | Ballato .................................. | 422/61 |
| 4,661,235 | 4/1987 | Krull et al. ........................... | 204/414 |
| 4,690,715 | 9/1987 | Allara et al. ..................... | 148/6.15 R |
| 4,776,944 | 10/1988 | Janata et al. ......................... | 204/415 |
| 4,812,221 | 3/1989 | Madou et al. ....................... | 204/412 |
| 4,837,715 | 6/1989 | Ungpiyakul et al. ................. | 364/552 |
| 4,842,783 | 6/1989 | Blaylock .............................. | 264/1.4 |
| 4,844,613 | 7/1989 | Batchelder et al. .................. | 356/318 |
| 4,851,816 | 7/1989 | Macias et al. ........................ | 340/573 |
| 4,877,747 | 10/1989 | Stewart ................................. | 436/525 |
| 4,895,017 | 1/1990 | Pyke et al. .............................. | 73/23 |
| 4,992,385 | 2/1991 | Godfrey ............................... | 436/525 |
| 5,023,053 | 6/1991 | Finlan ............................... | 422/82.05 |
| 5,035,863 | 7/1991 | Finlan et al. ....................... | 422/82.05 |
| 5,055,265 | 10/1991 | Finlan ............................... | 422/82.05 |
| 5,057,560 | 10/1991 | Mueller ................................ | 524/22 |
| 5,063,081 | 11/1991 | Cozzette et al. .......................... | 427/2 |
| 5,064,619 | 11/1991 | Finlan ............................... | 422/82.05 |
| 5,076,094 | 12/1991 | Frye et al. ........................... | 73/19.03 |
| 5,096,671 | 3/1992 | Kane et al. ........................ | 422/820.7 |
| 5,114,676 | 5/1992 | Leiner et al. ..................... | 422/82.06 |
| 5,134,057 | 7/1992 | Kuypers et al. ..................... | 430/325 |
| 5,143,854 | 9/1992 | Pirrung et al. ....................... | 436/518 |
| 5,152,758 | 10/1992 | Kaetsu et al. ..................... | 604/890.1 |
| 5,155,791 * | 10/1992 | Hsiung ............................... | 385/122 |
| 5,182,135 | 1/1993 | Giesecke et al. ...................... | 427/98 |
| 5,189,902 | 3/1993 | Groeninger ......................... | 73/24.06 |
| 5,190,350 | 3/1993 | Backman ............................. | 436/501 |
| 5,235,238 | 8/1993 | Nomura et al. ...................... | 310/349 |
| 5,242,828 | 9/1993 | Bergstrom et al. .................. | 435/291 |
| 5,268,306 | 12/1993 | Berger ................................. | 436/527 |
| 5,280,548 | 1/1994 | Atwater et al. ....................... | 385/12 |
| 5,304,293 | 4/1994 | Tierney et al. ...................... | 204/414 |
| 5,327,225 | 7/1994 | Bender et al. ....................... | 356/445 |
| 5,334,303 | 8/1994 | Muramatsu et al. ................. | 204/412 |
| 5,352,582 * | 10/1994 | Lichtenwalter et al. ................. | 430/2 |
| 5,369,717 | 11/1994 | Attridge ............................... | 385/12 |
| 5,374,563 | 12/1994 | Maule .................................. | 436/165 |
| 5,376,255 | 12/1994 | Gumbrecht et al. ................. | 204/426 |
| 5,402,075 | 3/1995 | Lu et al. .............................. | 324/664 |
| 5,404,756 | 4/1995 | Briggs et al. ........................ | 73/718 |
| 5,415,842 | 5/1995 | Maule .............................. | 422/82.05 |
| 5,418,136 | 5/1995 | Miller .................................... | 435/5 |
| 5,430,815 | 7/1995 | Shen et al. ............................ | 385/13 |
| 5,436,161 | 7/1995 | Bergstrom et al. .................. | 435/291 |
| 5,451,683 | 9/1995 | Barrett et al. ........................ | 436/518 |
| 5,455,475 | 10/1995 | Josse et al. .......................... | 310/316 |
| 5,482,830 | 1/1996 | Bogart et al. ........................... | 435/5 |
| 5,482,867 | 1/1996 | Barrett et al. ........................ | 436/518 |
| 5,489,678 | 2/1996 | Fodor et al. ........................ | 536/22.1 |
| 5,489,988 | 2/1996 | Ackley et al. ....................... | 356/436 |
| 5,492,840 | 2/1996 | Malmqvist et al. .................. | 436/518 |
| 5,510,481 | 4/1996 | Bednarski ............................ | 536/120 |
| 5,512,131 | 4/1996 | Kumar et al. ..................... | 156/655.1 |
| 5,514,501 | 5/1996 | Tarlov .................................... | 430/5 |
| 5,514,559 | 5/1996 | Markert-Hahn et al. ............ | 435/7.92 |
| 5,527,711 | 6/1996 | Tom-Moy et al. ................... | 436/518 |
| 5,554,541 | 9/1996 | Malmqvist et al. ................. | 436/518 |
| 5,568,606 | 10/1996 | Dobbek ......................... | 395/182.06 |
| 5,620,850 | 4/1997 | Bamdad et al. ..................... | 530/300 |
| 5,643,681 | 7/1997 | Voorhees et al. .................... | 428/483 |
| 5,658,443 | 8/1997 | Yamamoto et al. ................. | 204/403 |
| 5,717,453 * | 2/1998 | Wohlstadter .......................... | 348/56 |
| 5,922,550 * | 7/1999 | Everhart et al. ..................... | 435/7.21 |
| 6,020,047 * | 2/2000 | Everhart .............................. | 428/209 |

OTHER PUBLICATIONS

Josse et al., "Electrical Surface Perturbation of a Piezoelectric Acoustic Plate Mode by a Conductive Liquid Loading", IEEE Transactions on Ultrasonics, Ferroelectrics, and Frequency Control, vol. 39, No. 4, (Jul. 1992).

Josse et al., "On the use of ZX–LiNbO3 acoustic plate mode devices as detectors for dilute electrolytes", Sensors and Actuators B, vol. 9, pp. 97–112 (1992).

Daphint et al., "Probing of strong and weak electrolytes with acoustic wave fields", Sensors and Actuators B, vol. 9, pp. 155–162 (1992).

Kumar et al., "Patterning Self–Assembled Monolayers: Applications in Materials Science", Langmuir, vol. 10, pp. 1498–1511 (1994).

Seah, M.P. "Quantitative Prediction of Surface Segregation", Journal of Catalysis, vol. 57, pp. 450–457 (1979).

Tsai et al., "Comment on the Prediction of Segregation to Alloy Surfaces", Journal of Catalysis—Letters to the Editor, vol. 50, pp. 200–202 (1977).

Burton et al. "Prediction of Segregation to Alloy Surfaces from Bulk Phase Diagram", Phys. Rev. Letter, vol. 37, No. 21, pp. 1433–1436 (Nov. 22, 1976).

Johnson et al. "Orientation dependence of surface segregation in a dilute Ni–Au alloy", J. Vac. Sci. Technol., vol. 15, No. 2, pp. 467–469 (Mar./Apr. 1978).

Osada et al., "Intelligent Gels", Scientific American, pp. 82–87, May 1993.

Saito et al., "Volume Phase Transition of N–Alkylacrylamide Gels", Advances on Polymer Science, vol. 109, pp. 207–232 (1993).

Okano T. "Molecular Design of Temperature–Responsive Polymers as Intelligent Materials", Advances in Polymer Science, vol. 110, pp. 179–197 (1993).

Shibayama et al., "Volume Phase Transition and Related Phenomena of Polymer Gels", Advances in Polymer Science, vol. 109, pp. 1–62 (1993).

Kokufuta, E. "Novel Applications for Stimulus–Sensitive Polymer Gels in the Preparation of Functional Immobilized Biocatalysts", Advances in Polymer Science, vol. 110, pp. 157–177 (1993).

Osada et al, "Stimuli–Responsive Polymer Gels and Their Application to Chemomechanical Systems", Prog. Polym. Sci., vol. 18, pp. 187–226 (1993).

Irie, M. "Stimuli–Responsive Poly(N–isopropylacrylamide) Photo–and Chemical–Induced Phase Transitions", Advances in Polymer Science, vol. 110, pp. 49–65 (1993).

Mrksich et al., "Patterning self–assembled monolayers using microcontact printing: A new technology for biosensors?", Tibtech, vol. 13, pp. 228–235 (1995).

Abbottt et al., Using Micromachining, Molecular Self–Assembly, and Wet Etching to Fabricate 0.1–1 $\mu$m–Scale Structures of Gold and Silicon, Chemistry of Materials, vol. 6, No. 5, pp. 596–602 (1994).

Jeon et al., "Patterned Self–Assembled Monolayers Formed by Microcontact Printing Direct Selective Metalization by Chemical Vapor Deposition on Planar and Nonplanar Substrates", Langmuir, vol. 11, No. 8, pp. 3024–3026 (1995).

Kim et al., "Combining Patterned Self–Assembled Monolayers of Alkanethiolates on Gold with Anisotropic Etching of Silicon to Generate Controlled Surface Morphologies", J. Electrochem. Soc., vol. 142, No.2, pp. 628–633 (Feb. 1995).

Folkers et al., "Self–Assembled Monolayers of Long–Chain Hydroxamic Acids on the Native Oxides of Metals", Langmuire, vol. 11, No. 3, pp. 813–824 (1995).

Kumar et al., "Patterned Condensation Figures as Optical Diffraction Gratings", Science, vol. 263, pp. 60–62 (Jan. 7, 1994).

Wilbur et al., "Microfabrication by Microcontact Print of Self–Assembled Monolayers", Adv. Mater., vol. 6, No. 7/8, pp. 600–604 (1994).

Responsive Gels: Volume Transitions I, vol. 109: Advances in Polymer Science, Dusek, K. ed., Springer–Verlag, Berlin, 1993.

Responsive Gels: Volume Transitions II, vol. 110: Advances in Polymer Science, Dusek, K. ed., Springer–Verlag, Berlin, 1993.

Patent Abstracts of Japan, JP 05 132640 (Ricoh Co. Ltd.) (May 28, 1993).

Patent Abstracts of Japan, JP 02 085755 (Teijin Ltd.) (Mar. 27, 1990).

Copy of Search Report for PCT/US97/08522 dated Aug. 8, 1997.

R. Block et al., "Mechanical resonance gas sensors with piezoelectric excitation and detection using PVDF polymer foils", Sensors and Actuators, vol. B7, Mar. 1992, pp. 596–601.

S.J. Martin, "Sensing liquid properties with thickness–shear mode resonators", Sensors and Actuators A, vol. A44, Sep. 1994, pp. 209–218.

Abstract of EP 0 453 820 dated Oct. 30, 1991.

Abstract of WO 96/26435 dated Aug. 29, 1996.

Muller, W. et al., Science, vol. 262, Dec. 10, 1993, pp. 1706–1708.

Jennane, J. et al. Can. J. Chem. vol. 74, 1996, pp. 2509–2517.

Diamandis, EP et al., *Clin. Chem.*, vol. 37(5), 1991, pp. 625–633.

Bhatia, S.K. et al., 1992, *J. Am. Chem. Soc.*, vol. 114, p. 4432.

Bhatia, S.K. et al., Analytical Biochem., vol. 208, pp. 197–205, 1993.

Häussling, L. et al., Angew Chem. Int. Ed. Engl., vol. 30, No. 5, 1991, pp. 569–572.

Larsen N.B. et al., "Order in Microcontact Printed Self–Assembled Monolayers", *J. Am. Chem. Soc.* vol. 119, pp. 3017–3026, 1997.

* cited by examiner

Topography Image

Lateral Force Image

3D Graphic of Topography Image

High resolution printer film output     Gel on metallized MYLAR

A. High-Resolution Printer film

B. Photoresist master on gold film

C. Elastomeric Stamp

D. Gel on metallized MYLAR

GEL SENSORS AND METHOD OF USE THEREOF

TECHNICAL FIELD

The present invention is in the field of sensors, and more specifically in the field of gel sensors which rely on optical diffraction as the sensing mechanism.

BACKGROUND OF THE INVENTION

Microcontact printing is a technique for forming patterns of organic monolayers with micrometer and submicron lateral dimensions. It offers experimental simplicity and flexibility in forming certain types of patterns. It relies on the remarkable ability of self-assembled monolayers of long-chain alkanethiolates to form on gold and other metals. These patterns can act as nanometer resists by protecting the supporting metal from corrosion by appropriately formulated etchants, or, can allow for the selective placement of fluids on hydrophilic regions of the pattern. Patterns of self-assembled monolayers having dimensions that can be less than 1 $\mu$m are formed by using the alkanethiol as an "ink", and by printing them on the metal support using an elastomeric "stamp". The stamp is fabricated by molding a silicone elastomer using a master prepared by optical or X-ray microlithography or by other techniques.

Microcontact printing of patterned self-assembled monolayers brings to microfabrication a number of new capabilities. First, microcontact printing makes it possible to form patterns that are distinguished only by their constituent functional groups; this capability permits the control of surface properties such as interfacial free energies with great precision. Second, because microcontact printing relies on molecular self-assembly, it generates a system that is (at least locally) close to a thermodynamic minimum and is intrinsically defect-rejecting and self-healing. Simple procedures, with minimal protection against surface contamination by adsorbed materials or by particles, can lead to surprisingly low levels of defects in the final structures. The procedure can be conducted at atmospheric pressure, in an unprotected laboratory atmosphere. Thus, microcontact printing is especially useful in laboratories that do not have routine access to the equipment normally used in microfabrication, or for which the capital cost of equipment is a serious concern. Third, the patterned self-assembled monolayers can be designed to act as resists with a number of wet-chemical etchants.

Working with liquid etchants suffers from the disadvantages of handling solvents and disposing of wastes, but also enjoys substantial advantages: a high degree of control over contamination of surfaces; reduced damage to the substrate from energetic interactions with atoms or ions; the ability to manipulate complex and sensitive organic functionalities. Because the self-assembled monolayers are only 1–3 nm thick, there is little loss in edge definition due to the thickness of the resist; the major determinants of edge resolution seem to be the fidelity of the contact printing and the anisotropy of etching the underlying metal. In the current best cases, features of size 0.2 $\mu$m can be fabricated; edge resolution in systems showing this resolution in thickness is less than 50 nm.

Gels are cross-linked networks of polymers swollen with a liquid. Softness, elasticity, and the capacity to store a fluid make gels unique materials, and soft and gentle materials are beginning to replace some of the hard mechanical materials in various industries.

Due to the cross-linking, various properties of individual polymers become visible on a macroscopic scale. The polymer network changes its volume in response to a change in environment: temperature, solvent composition, mechanical strain, electric field, exposure to light, pH, salt concentration, etc. *Advances in Polymer Science*, ed. K. Dusek, Vol. 109, p. v (Springer-Verlag New York 1993); S. Saito, pp. 207–232, Id.; M. Shibayama and T. Tanaka, pp. 1–62, Id.; Y. Osada, et al., pp. 82–87, *Scientific American* (May 1993); Y. Osada and J. Gong, *Prog. Polym. Sci.*, vol. 18, pp. 187–226 (Great Br. 1993); Irie, M., pp. 49–65 in *Advances in Polymer Science*, ed. K. Dusek, Vol. 110 (Springer-Verlag New York 1993); E. Kokufuta, pp. 157–77, Id.; T. Okano, pp. 179–197, Id., all incorporated by reference.

Hydrophilic gels in aqueous solution have been the most widely studied, but almost any polymer can be cross linked to form a gel which will swell in a sufficiently good quality solvent. The three-dimensional network is stabilized by cross links which may be provided by covalent bonds, physical entanglements, crystallites, charge complexes, hydrogen bonding, van der Waal's or hydrophobic interactions. Gels have many technologically important roles in chemical separations, biomedical devices and absorbent products, to name a few areas. The properties that make gels useful include their sorption capacities, swelling kinetics, permeabilities to dissolved solutes, surface properties (e.g., adhesiveness), mechanical characteristics, and optical properties. The single most important property of a gel is its swelling degree, since most of the properties are directly influenced by this. S. H. Gehrke, p. 85, in *Advances in Polymer Science*, ed. K. Dusek, Vol. 110 (Springer-Verlag New York 1993).

"Responsive" polymer gels are materials whose properties, most notably their solvent-swollen volumes, change in response to specific environmental stimuli including temperature, pH, electric field, solvent quality, light intensity and wavelength, pressure, ionic strength, ion identity, and specific chemical triggers, like glucose. S. Saito, pp. 207–232; M. Shibayama and T. Tanaka, pp. 1–62. The property which often changes the most dramatically is the swollen volume. These changes may occur discontinuously at a specific stimulus level (a phase transition), or gradually over a range of stimulus values. All of these changes are reversible with no inherent limit in lifetime.

Gels have been employed as chemical sensing surfaces, for example, in conjunction with fiber-optic systems, or elaborate mechanical or electrode systems. These systems are often quite elaborate, and suffer either from lack of flexibility or expense, or both. For example, U.S. Pat. No. 5,436,161 to J. Bergstrom, et al., discloses a matrix coating for surface plasmon resonance detection, to be used with a rigid dielectric material, such as a glass plate.

The information-carrying capacity of light provides an elegant method for detecting and displaying information in a way that is readily interpreted by a human. Sensors that visibly change color in response to a surface antibody-antigen binding reaction are already commercially available. An example of such a device, based on thin film interference, is the group B streptococcal antigen detector made by Biostar™ [G. R. Bogart, et al., "Devices and methods for detection of an analyte based upon light interference," U.S. Pat. No. 5,482,830, (Assignee: Biostar, Inc. Boulder, Colo.)]. Another example of a very simple optical-based sensor is where a Bragg reflector expands in the presence of water to change the reflected wavelength. The detection and display components both device are integrated so that an electronic display (with associated power supply and processing circuit) is not needed.

However, that sort of detection device is suitable only for a narrow range of sensor applications. There is a need for a sensor technology platform that can be slightly modified to accommodate a wide range of stimuli and sensing conditions. There is a need, therefore, for a simple sensing system that takes full advantage of the responsive properties of gels, but which is flexible, easy to use, and preferably, disposable.

SUMMARY OF THE INVENTION

The present invention comprises an optically diffracting sensing device in which a diffraction pattern changes upon exposure to a predetermined stimuli. The diffraction pattern in the sensing device of the present invention may be two or three dimensional, and, in one embodiment, the change in diffraction patterns is recognizable to the untrained eye. The sensing device of the present invention comprises one or more gels coated onto patterned, self-assembling monolayers of alkanethiolates, carboxylic acids, hydroxamic acids, or phosphonic acids printed onto a variety of substrates, including, but not limited to, glass, silicon, aluminum oxide, and thermoplastic films metallized with gold, or with an alloy such as nickel/gold. The present invention also comprises the method of making this device, and the use of this device. In its desired embodiment, the sensing device of the present invention uses white light without any supporting detection or amplification systems.

Patterned self-assembling monolayers allow for the controlled placement of gel solutions thereon and which can contain a chemically reactive, indicator functionality. The gels suitable for use in the present invention can be produced by a variety of means, including solvent evaporation, radiation, or chemical cross-linking. When exposed to electromagnetic radiation, such as visible light, the sensing devices of the present invention produce optical diffraction patterns which can change depending on the reaction of the gel with the stimulus of interest. The electromagnetic radiation can be in the visible spectrum, and can be either reflected from the substrate, or transmitted through the substrate. The stimulus to be detected can be any compound that reacts with the gel directly or with an indicator substance contained in the gel. (See, for example, Irie, M., pp. 49–65; Y. Osada and J. Gong) The present invention can be used to measure any stimuli to which a gel will respond, including, but not limited to, mechanical, temperature, electrical, and chemical stimuli.

These and other objects, features and advantages of the present invention will become apparent after a review of the following detailed description of the disclosed embodiments.

BRIEF DESCRIPTION OF THE FIGURES

FIG. 3b is a photograph of the diffraction pattern formed by visible light shown through the self-assembling monolayer pattern described by FIG. 3a.

DETAILED DESCRIPTION

Figure 1:
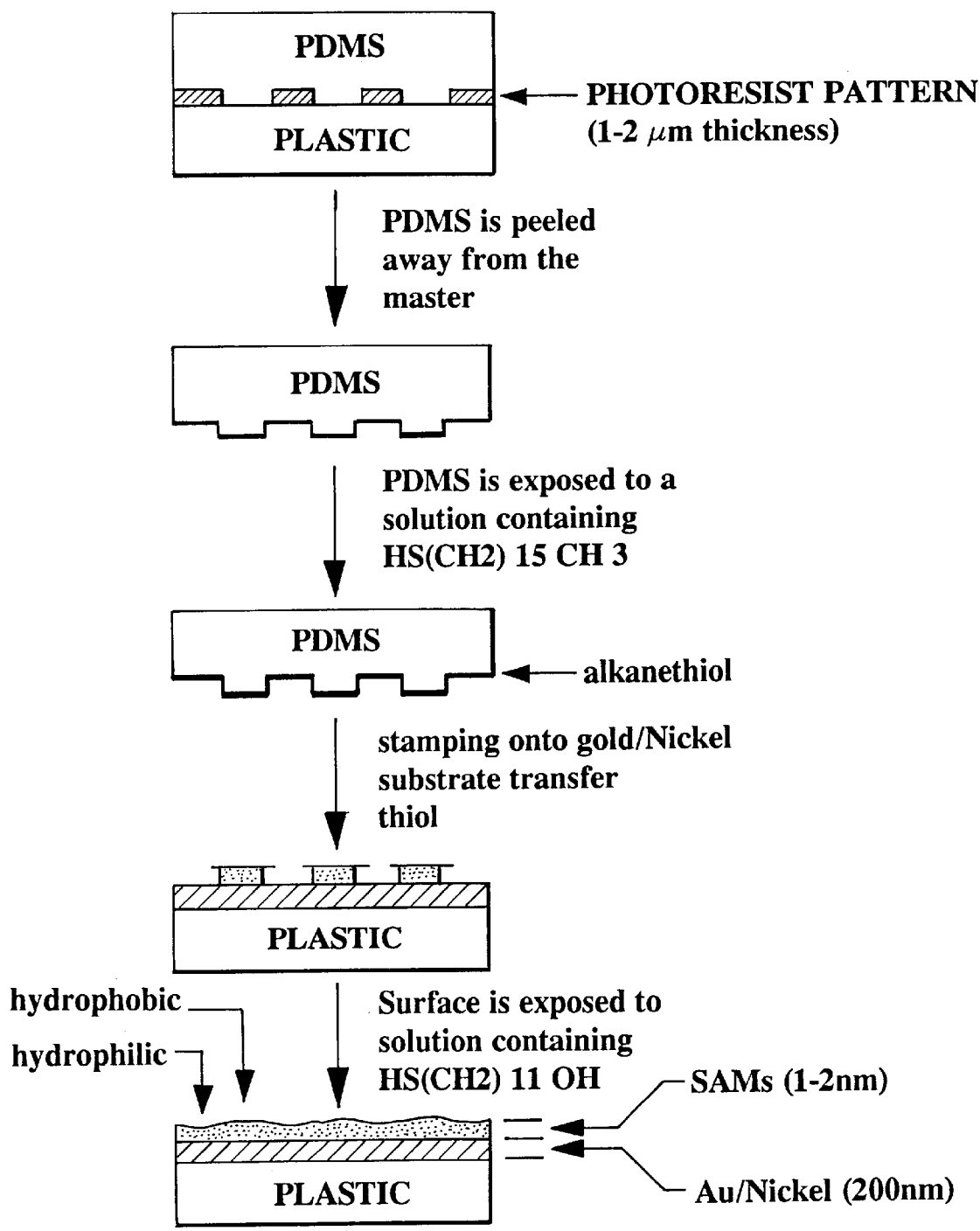
FIG. 1 is a schematic of contact printing of self-assembling monolayers, using a nickel/gold coated polymer substrate as an example. A polydimethylsiloxane (PDMS; silicone elastomer 184; Dow Corning Corp., Midland, Mich.) is polymerized on a silicone master containing a pre-determined pattern. The PDMS is peeled away from the master, and then exposed to a solution containing $HS(CH_2)_{15}CH_3$. The alkane-thiol coated stamp is then stamped onto the nickel/gold-coated substrate. Then, the surface of the substrate is exposed to a solution containing a different alkane thiol such as $HS(CH_2)_{11}OH$.

The present invention comprises an optically diffracting sensing device in which the diffraction pattern changes upon exposure to predetermined stimuli. The diffraction pattern may be two or three dimensional and, in one embodiment, the change in diffraction patterns is recognizable to the unaided eye. The sensing device of the present invention further comprises one or more gels coated onto patterned, self-assembling monolayers of, for example, alkanethiolates, carboxylic acids, hydroxamic acids, or phosphonic acids printed onto a variety of substrates including, but not limited to, glass, silicon, aluminum oxide, and thermoplastic films metallized with gold, or with an alloy such as nickel/gold. Other substrates that can be used according to the present invention include, but are not limited to, $CrO_x$, $CuO_x$, $AgO_x$, platinum, and lead. The gels used according to the present invention are capable of responding to the presence or change in stimuli. Usually the response is a change in volume, shape, color or a change in refractive index. The stimuli can be a chemical compound or a physical parameter such as environment: temperature, solvent composition, mechanical strain, electric field, exposure to light, pH, salt concentration, solvent quality, light intensity and wavelength, pressure, ionic strength, ion identity, and specific chemical triggers, e.g., glucose. The present invention also comprises the method of making the sensing device and the use of this device.

Patterned self-assembling monolayers allow for the controlled placement of the gel thereon. The term "patterned self-assembling monolayers thereon" as used herein means the self-assembling monolayers in any pattern on the metallized polymer films including a solid pattern. The optical sensing devices of the present invention produce optical diffraction patterns which differ depending on the reaction of the self-assembling monolayer and the gel with the stimulus of interest. The electromagnetic radiation that is diffracted is preferably in the visible spectrum, and can be either reflected from the substrate or transmitted through the substrate. The stimulus to be measured by the sensing device of the present invention can be any substance or physical parameter that interacts with the gel or with an analyte in the gel. It is contemplated as part of the invention that the gel can contain an analyte that will react with a stimulus thereby causing the gel to change in volume, shape, color or refractive index. Thus, it can be the gel interacting directly with the stimulus or the gel can contain an analyte that reacts with the stimulus.

Microcontact printing is a technique for forming patterns of organic monolayers with micron or submicron lateral dimensions. It offers experimental simplicity and flexibility in forming certain types of patterns. It relies on the remarkable ability of self-assembled monolayers of long-chain alkanethiolates to form on gold and other metals. These patterns can act as nanometer resists by protecting the supporting substrate from corrosion by appropriately formulated etchants, or, can allow for the selective placement of fluids on hydrophilic regions of the pattern. Patterns of self-assembled monolayers having dimensions that can be less than 1 μm are formed by using the alkanethiol as an "ink", and by printing them on the metal support using an elastomeric "stamp". The stamp is fabricated by molding a silicone elastomer using a master prepared by optical or X-ray microlithography or by other techniques.

Microcontact printing of patterned self-assembled monolayers brings to microfabrication a number of new capabilities. First, microcontact printing makes it possible to form patterns that are distinguished only by their constituent functional groups; this capability permits the control of surface properties such as interfacial free energies with great precision. Second, because micro-contact printing relies on molecular self-assembly, it generates a system that is (at least locally) close to a thermodynamic minimum and is intrinsically defect-rejecting and self-healing. Simple procedures, with minimal protection against surface contamination by adsorbed materials or by particles, can lead to surprisingly low levels of defects in the final structures. The procedure can be conducted at atmospheric pressure, in an unprotected laboratory atmosphere. Thus, microcontact printing is especially useful in laboratories that do not have routine access to the equipment normally used in microfabrication, or for which the capital cost of equipment is a serious concern. Third, the patterned self-assembled monolayers can be designed to act as resists with a number of wet-chemical etchants.

Because the self-assembled monolayers are only 1–3 nm thick, there is little loss in edge definition due to the thickness of the resist; the major determinants of edge resolution seem to be the fidelity of the contact printing and the anisotropy of etching the underlying metal. In the current best cases, features of size 0.2 µm can be fabricated; edge resolution in systems showing this resolution in thickness is less than 50 nm.

Figure 8:
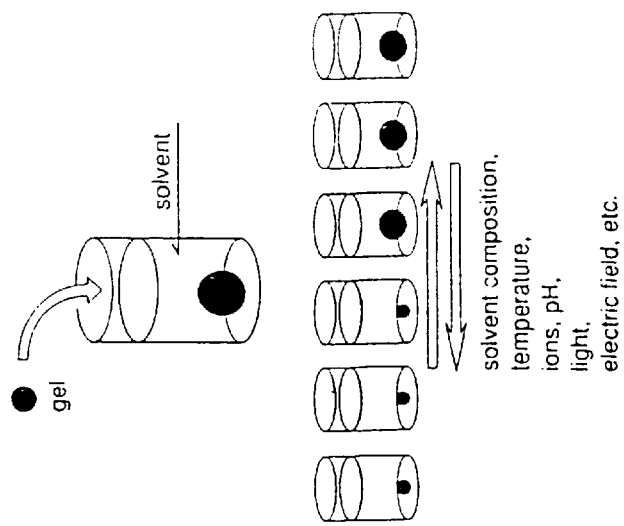
FIG. 8, shows a graph of a temperature induced volume transition in a gel, where the ordinate gives the temperature in degrees Celsius, and the abscissa gives the ratio of resultant volume to original volume. The right hand side of FIG. 8 is a schematization of a volume change of a gel due to factors such as solvent composition, temperature, ions, pH, light, and electric field.
Figure 8:
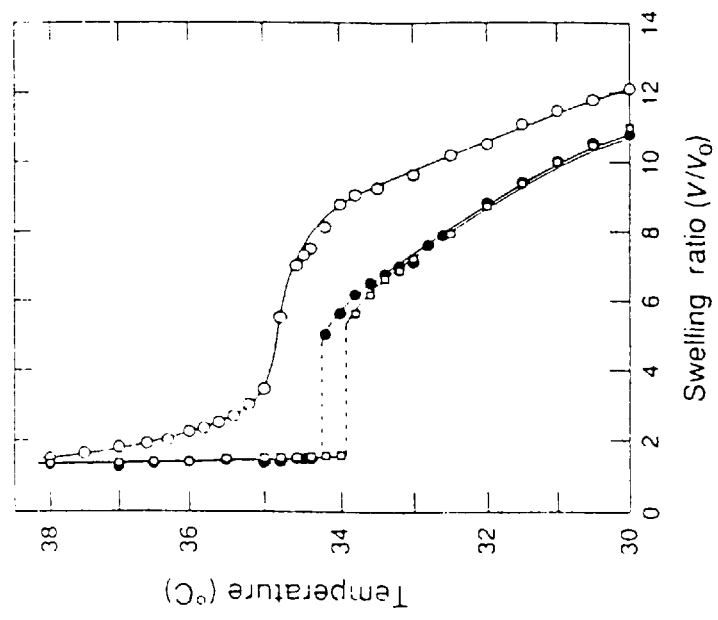

Gels, as used in the present invention, have both liquid-like and solid-like properties. The liquid-like properties result from the fact that the major constituent of gels is usually a liquid, e.g., water. For example, a jelly consists of approximately 97% water and 3% gelatin. On the other hand, a gel can retain its shape since it has a shear modulus which becomes apparent when the gel is deformed. The modulus is due to the cross-linking of the polymers in the form of a network. These aspects of a gel represent the solid nature of gels. In addition to these liquid- and solid-like aspects, a gel can change its state drastically, similar to the way a gas changes its volume more than a thousand fold. Two states of gels; the collapsed and swollen states, correspond to the liquid and the gas states of fluids respectively. FIG. 8 shows a graph of a temperature induced volume transition in a gel, where the ordinate gives the temperature in degrees Celsius, and the abscissa gives the ratio of resultant volume to original volume. As can be seen by the graph, a sharp volume transition occurs for this gel between 34 and 36 degrees Celsius. The right hand side of FIG. 8 is a schematization of a volume change of a gel due to factors such as solvent composition, temperature, ions, pH, light, and electric field.

A gel can be viewed as a container of solvent made of a three dimensional mesh. In a dried state, a gel is a solid material. However, a gel swells until it reaches the swelling equilibrium when a solvent is added. The solvent molecules are kept in the three dimensional mesh and the combination of the mesh and the solvent molecules creates a "world" having characteristic properties. This world can be either isolated from (isochore) or linked to (isobar) its surrounding world by changing the population, i.e., the solvent molecules.

A gel can be a "single polymer molecule". The term "single polymer molecule" means that all the monomer units in a one piece of gel are connected to each other and form one big molecule on a macroscopic scale. Because of this nature, a gel is a macroscopic representation of single polymer behavior.

Many kinds of external stimuli, such as, temperature, pH, photons, ions, electric current (field), etc., can control the volume of the gel. Particularly, in the case of volume phase transition, an enormous change in volume can be induced by an infinitesimal change of one of the these stimuli, and this is of great importance in the present invention, as an actuator, sensor, switching device and so on. See FIG. 8. These volume phase transitions can be induced by van der Waal's, hydrophobic, hydrogen bonding, electrostatic, and charge-transfer interactions.

In the present invention, the gel is coupled to the self-assembling monolayer printed as described above. Depending upon the property to be sensed, the gel includes, but is not limited to, a polysaccharide such as agarose, dextran, carageenan, alginic, acid, starch, cellulose, deionized gelatin, and derivatives of these such as carboxymethyl derivatives. The gel may also be a water-swellable organic polymer such as polyvinyl alcohol, polyacrylic acid, polyacrylamide, or polyethylene glycol. Aqueous gels are also known in the art as "hydrogels", and "hydrophilic polymers". They may be copolymers or homopolymers. Suitable copolymers may either be regular copolymers containing substantially no other material in their matrices, or they may be copolymers which contain monomers such as styrene and vinyl acetate, for example. Examples of suitable copolymers which may or may not contain monomers include, but are not limited to, N-vinyl pyrrolidone and glycidyl methacrylate.

Homopolymers include those that are slightly cross-linked, such as hydroxyethyl methacrylate. Suitable copolymers with or without monomers and homopolymers may also be polymerized from the following non-limiting list of monomers: hydroxyalkyl acrylates and hydroxyalkyl methacrylates, for example, hydroxyethyl acrylate, hydroxypropyl acrylate, and hydroxybutyl methacrylate; epoxy acrylates and epoxy methacrylates, such as, glycidyl methacrylate; amino alkyl acrylates and amino alkyl methacrylates; N-vinyl compounds, such as, for example, N-vinyl pyrrolidone, N-vinyl carbazole, N-vinyl acetamide, and N-vinyl succinimide; amino styrenes; polyvinyl alcohols and polyvinyl amines; polyacrylamides such as N-isopropyl acrylamide and various substituted polyacrylamides; vinyl pyridine; vinyl sulfonate and polyvinyl sulfate; vinylene carbonate; vinyl acetic acid, and vinyl crotonic acid; allyl amine and allyl alcohol; and vinyl glycidyl ethers.

Polymer gels swollen in nonvolatile organic solvents are known as organogels. A few examples of organogels are systems based on aluminum stearate, oleate, or naphthenate. These polymers form non-aqueous gels on cooling with hydrocarbons. Electroconductive organogels have also been prepared from 3-alkyl thiophenes using $FeCl_3$ as a catalyst. These polymer gels exhibit drastic volume changes when the solvent composition of ethanol-chloroform was changed. The absorption spectrum also changes in association with the volume change and temperature. Another type of electroconductive gel consists of an electrodonating polymeric network and a low molecular weight acceptor subsequently doped to the gel. Thus, a 7,7,8,8-tetracyanoquinodimethane (TCNQ) was doped as an electron acceptor into a cross linked polymeric donor: poly [N-[3-(dimethylamino)propyl] acrylamide] (PDMAPAA) in dimethylformamide (DMF). When TCNQ was doped, a significant swelling and coloration due to the formation of a charge-transfer (CT) complex occurred.

The gel can be derivatized to contain hydroxyl, carboxyl, amino, aldehyde, carbonyl, epoxy, or vinyl groups for immobilizing a desired ligand, and optionally, a biospecific ligand bound via said groups. Many examples of suitable gels may be found in Hydrogels in Medicine and Pharmacy, vols. I–III, ed. Peppas, N. A. (CRC Press 1986-7), and *Advances in Polymer Science,* ed. K. Dusek, vols. 109, 110 (Springer-Verlag New York 1993), and references cited therein, all incorporated herein by reference.

Examples of derivatization of gels may be found in U.S. Pat. No. 5,436,161 to J. Bergstrom, which is incorporated herein by reference. In one embodiment of the present invention, the desired ligand might be an antibody, a T or B cell receptor, an epitope, or a fragment of any of the foregoing including, but not limited to, molecules, such as proteins, glycoproteins, metal salts, ions, and the like. The gel may also include neurotransmitters, hormones, growth factors, cytokines, monokines, lymphokines, nutrients, enzymes, and receptors. Also included are structured elements such as macromolecular structures, organelles and cells, including, but not limited to, cells of ectodermal, mesodermal, and endodermal origin such as stem cells, blood cells, neural cells, immune cells, and gastrointestinal cells, and also microorganisms, such as fungi, viruses, bacteria and protozoa. Many of these gel encapsulated cells can produce a volume changing stimulus when exposed to specific analytes.

In one embodiment of the present invention, a hydrazide function is created in the dextran matrix for binding ligands containing aldehyde groups, for example antibodies, in which the carbohydrate chain has been oxidized so that it then contains an aldehyde function. In this instance, the dextran matrix is initially modified with carboxymethyl groups which are partly reacted to form hydrazide groups. With this activated matrix at least two important advantages are obtained: (1) This matrix contains unreacted carboxyl groups which in low ionic strength conditions will act as ion exchangers, and by electrostatic interaction the ligand which is to be immobilized is connected to the dextran matrix; (2) This matrix will very efficiently bind the ligand thus concentrated at the surface, viz. by condensation of ligand aldehyde groups with the hydrazide function of the matrix.

According to another embodiment of the present invention, a part of the carboxyl groups in carboxymethyl-modified dextran are modified so as to give reactive ester functions, e.g., by treatment with an aqueous solution of N-hydroxysuccinimide and N-(3-dimethyl-aminopropyl)-N'-ethylcarbodiimide hydrochloride. In the same way as in the example described above, the residual charges, i.e., unreacted carboxyl groups, will contribute to effecting a concentration of ligands on the surface. Ligands containing amine groups such as, for example, proteins and peptides, may then be coupled to the dextran matrix by covalent bonds.

According to an alternative procedure, the aforesaid reactive ester is utilized for reaction with a disulfide-containing compound such as, for instance, 2-(2-pyridinyldithio) ethanamine: in this manner a matrix is obtained which contains disulfide groups, and these can be employed for coupling thiol-containing ligands such as, for example, reduced F(ab) fragments of immunoglobulins (see Brocklehurst, K., et al., J. Biochem., vol. 133, p. 573, et seq. (1973), incorporated herein by reference). After cleavage of the disulfide bonds, for instance, by reduction or thioldisulfide exchange, the thiol modified surface formed can be used for coupling of a disulfide-containing ligand such as, for instance, N-succinimidyl 3-(2-pyridinyldithio) propionate (SPDP) modified proteins.

The advantage of this procedure is that the ligands via, for example, a reduction step can be cleaved off to give a sensing surface with reactive thiols. This thiol-modified surface can, in an analogous procedure, be used for renewed covalent coupling of thiol- or disulfide-containing ligands. In this way the capability of chemical regeneration of the sensing surface can be obtained, which can be used for general utilization of the same surface for couplings of several different ligands. The procedure can also be used when, for example, a biological interaction is studied, and this interaction cannot be broken while retaining biological activity of the immobilized ligand.

One important aspect of the present invention is that one or more of the layers forming the sensing surface to be used in a given analysis can be synthesized and/or functionalized in situ by adding the appropriate reagents to the surface in a flow-through cell in a biosensor system.

In summary, there are a multitude of ligands that can be employed for the detection of biomolecules by means of interacting therewith. It will be readily evident that ion exchanging groups, metal chelating groups and various types of receptors for biological molecules—known from conventional liquid chromatographic procedures—may be employed for the construction of systems which are suitable for selection purposes, even in complex measuring systems.

Metallo-organic materials, such as metallophthalocyanine, may also be included in the gel. Other substances, such as surfactants, inorganic salts, e.g., NaBr, KBr, NaCl, KCl, NaI, and KI, polar organic additives, such as methanol and glycerol, tetra-alkylammonium bromides, and crown ethers, e.g., benzo[18]crown-6, may be added to the gel to affect its swelling characteristics. Saito, Konno & Inomata; Irie. Light sensitive compounds, such as azobenzene chromophores, can be added to the gel to affect its characteristics.

The gel used in the present invention may also be made in a gradient arrangement, as set forth in "Molecular Gradients of Substituted Alkanethiols on Gold: Preparation and Characterization", by Bo Liedberg and Pentti Tengvall, published in Langmuir, Vol. 11, No. 10, 1995, pp. 3821–3827.

When the substrate with the gel atop the self-assembling monolayers is exposed to a stimulus or analyte that is capable of reacting with or affecting the gel, the sensing device produces optical diffraction patterns which change from the original optical diffraction pattern, depending on the reaction of the gel on the self-assembling monolayer with the stimulus of interest. It is to be understood that more than one self-assembling monolayer can be printed on a substrate thereby allowing one to associate the gel with one self-assembling monolayer and not with the second self-assembling monolayer.

Self-assembled monolayers of organic compounds on inorganic or metal surfaces are becoming increasingly important in many areas of materials science. Although there are many different systems of self-assembling monolayers based on different organic components and supports, desired systems are those of alkanethiolates, $HS(CH_2)_nR$. Typically, a gold film, 5 to 2000 nm thick, is supported on a titanium-primed $Si/SiO_2$ wafer or glass sheet. The titanium serves as an adhesion promoter between gold and the support. The alkanethiols chemisorb on the gold surface from a solution in which the gold film is immersed, and form adsorbed alkanethiolates with loss of hydrogen. Adsorption can also occur from the vapor. Self-assembling monolayers formed on gold from long-chain alkanethiolates of structure $X(CH_2)_nY$—$(CH_2)_mS$ are highly ordered and can be considered as crystalline or quasi-crystalline molecular arrays. A wide variety of organic functional groups (X, Y) can be incorporated into the surface or interior of the monolayer.

Self-assembling monolayers can therefore be tailored to provide a wide variety of material properties: wettability and protection against corrosion by chemical etchants are especially relevant to microcontact printing. In one embodiment of the present invention, there are two or more self-assembling monolayers with different chemical properties.

In another embodiment of the present invention, a first self-assembling monolayer is hydrophobic, and a second self-assembling monolayer is hydrophilic.

FIG. 1 outlines the procedure used for microcontact printing onto a substrate. An elastomeric stamp is used to transfer by contact alkanethiol "ink" to a surface coated with a metal alloy. In a desired embodiment, the alloy surface is predominantly gold. Preferred alloys are those such as nickel/gold, which are known to show an enrichment in the surface concentration of gold relative to its bulk concentration. Prediction of surface segregation of one metal of an alloy is described in M. P. Seah, "Quantitative Prediction of Surface Segregation," *Journal of Catalysis,* vol. 57, pp. 450–457 (1979), and J. J. Burton, et al., "Prediction of Segregation to Alloy Surfaces from Bulk Phase Diagrams," *Physical Review Letters,* vol. 37, No. 21, pp. 1433–1436 (Nov. 22, 1976), both incorporated herein by reference. In one embodiment of the invention, the metal alloy has surface enrichment of a metal reacting with the self-assembling monolayer. If the stamp is patterned, a patterned self-assembling monolayer forms. The stamp is fabricated by casting polydimethylsiloxane (PDMS) on a master having the desired pattern. Masters are prepared using standard photolithographic techniques, or constructed from existing materials having microscale surface features. These methods are disclosed in U.S. Pat. No. 5,512,131 and copending U.S. patent application Ser. No. 08/707,456 entitled, "Method of Contact Printing on Metal Alloy Coated Polymer Films," and the U.S. patent application entitled, "Method of Contact Printing on Gold Coated Films," filed Dec. 18, 1996, all of which are incorporated herein by reference.

In a typical procedure, a photolithographically produced master is placed in a glass or plastic Petri dish, and a 10:1 ratio (w:w or v:v) mixture or SYLGARD® silicone elastomer 184 and SYLGARD® silicone elastomer 184 curing agent (Dow Corning Corporation) is poured over it. The elastomer is allowed to sit for approximately 30 minutes at room temperature and pressure to degas, then cured for 1 to 4 hours at 60° C., and gently peeled from the master. "Inking" of the elastomeric stamp is accomplished by exposing the stamp to a 0.1 to 10 mM solution of alkanethiol in anhydrous ethanol, either by pouring the solution over the surface of the stamp, or by rubbing the stamp gently with a Q-TIP® that has been saturated with the inking solution. The stamp is allowed to dry until no liquid is visible by eye on the surface of the stamp (typically about 60 seconds), either under ambient conditions, or by exposure to a stream of nitrogen gas. Following inking, the stamp is applied to a metal alloy, e.g., nickel/gold surface. Very light hand pressure is used to aid in complete contact between the stamp and the surface. The stamp is then gently peeled from the surface. Following removal of the stamp, the surface is washed of excess thiol and the patterned metal alloy surface can be subjected to chemical etchants (see below) that selectively remove underivatized areas of the metal alloy surface, and if desired, the underlying support(s). Alternatively, further derivatization of unstamped areas can be accomplished, either by using a second stamp, or by washing the entire surface with a different alkanethiol.

The elastomeric character of the stamp is essential to the success of the process. Polydimethylsiloxane (PDMS), when cured, is sufficiently elastomeric to allow good conformal contact of the stamp and the surface, even for surfaces with significant relief; this contact is essential for efficient contact transfer of the alkanethiol "ink" to the alloy-coated film. The elastomeric properties of PDMS are also important when the stamp is removed from the master. If the stamp is rigid (as is the master) it is difficult to separate the stamp and master after curing without damaging one of the two substrates. PDMS is also sufficiently rigid to retain its shape, even for features with sub-micron dimensions. Patterns with lines as small as 200 nm in width have been generated. The surface of PDMS has a low interfacial free energy (y=22.1 dynes/cm), and the stamp does not adhere to the metal alloy coated film. The stamp is durable. The same stamp has been used up to 100 times over a period of several months without significant degradation in performance. The polymeric nature of PDMS also plays a critical role in the inking procedure by enabling the stamp to absorb the alkanethiol ink by swelling.

Microcontact printing on metal alloy surfaces can be conducted with a variety of alkanethiol "inks". Alkanethiols that do not undergo reactive spreading (after application to the metal alloy film) are required for formation of small features with high resolution. For stamping in air, one can use autophobic alkanethiols such as hexadecanethiol. Microcontact printing of other non-autophobic alkanethiols, for example, $HS(CH_2)_{15}COOH$, can be conducted by stamping under a liquid such as water. Patterned self-assembling monolayers of alkanethiols on metal alloy provide excellent resist character with a number of wet-chemical etchants. See U.S. Pat. No. 5,512,131 to A. Kumar and G. M. Whitesides, incorporated herein by reference.

In one embodiment of the present invention, the self-assembling monolayer is formed of a carboxy-terminated alkane thiol stamped with a patterned elastomeric stamp onto a nickel/gold-surfaced thermoplastic film such as MYLAR®. The stamp is inked with a solution of alkanethiol in ethanol, dried, and brought into contact with a surface of nickel/gold. The alkanethiol is transferred to the surface only at those regions where the stamp contacts the surface, producing a pattern of self-assembling monolayer which is defined by the pattern of the stamp. Optionally, areas of unmodified nickel/gold surface next to the stamped areas can be rendered hydrophobic by reaction with a methyl-terminated alkane thiol. The film is then contacted with a solution capable of forming a gel, e.g., an aqueous solution of N-isopropylacryamide: for example, to coat the film it may be drawn though a two phase system of water and toluene. The polymer then assembles onto the patterned, hydrophilic SAM, forming the sensing device of the present invention.

A desirable embodiment of the present invention is a thermoplastic film substrate upon which the SAM with the gel is placed. Any thermoplastic film upon which a metal substrate can be deposited is suitable for the present invention. These include, but are not limited to polymers such as: polyethylene-terephthalate (MYLAR®), acrylonitrile-butadiene-styrene, acrylonitrile-methyl acrylate copolymer, cellophane, cellulosic polymers such as ethyl cellulose, cellulose acetate, cellulose acetate butyrate, cellulose propionate, cellulose triacetate, cellulose triacetate, polyethylene, polyethylene-vinyl acetate copolymers, ionomers (ethylene polymers) polyethylene-nylon copolymers, polypropylene, methyl pentene polymers, polyvinyl fluoride, and aromatic polysulfones. Preferably, the plastic film has an optical transparency of greater than 80%. Other suitable thermoplastics and suppliers may be found, for example, in reference works such as the *Modern Plastics Encyclopedia* (McGraw-Hill Publishing Co., New York 1923–1996), incorporated herein by reference.

In one embodiment of the invention, the thermoplastic film with the metal coating thereon has an optical transparency of between approximately 5% and 95%. A more desired optical transparency for the thermoplastic film used in the present invention is between approximately 20% and 80%. In a desired embodiment of the present invention, the thermoplastic film has at least an approximately 80% optical transparency, and the thickness of the metal coating is such as to maintain an optical transparency greater than about 20%, so that diffraction patterns can be produced by either reflected or transmitted light. This corresponds to a metal coating thickness of about 20 nm. However, in other embodiments of the invention, the gold thickness may be between approximately 1 nm and 1000 nm.

The preferred metal alloy for deposition on the film is gold and another metal. However, alloys of silver, aluminum, copper, iron, zirconium, platinum, nickel may also be used. Preferred metals are ones that do not form oxides, and thus assist in the formation of more predictable self-assembling monolayers. Alloys such as Ni/Au, Pt/Au, and Cu/Au, which show surface enrichments of Au, are suitable.

In principle, any surface with corrugations of appropriate size could be used as masters. The process of microcontact printing starts with an appropriate relief structure, from which an elastomeric stamp is cast. This 'master' template may be generated photolithographically, or by other procedures, such as commercially available diffraction gratings. In one embodiment, the stamp may be made from polydimethylsiloxane.

In one embodiment of the present invention, the self-assembling monolayer has the following general formula:

$$X-R-Y$$

X is reactive with metal or metal oxide. For example, X may be asymmetrical or symmetrical disulfide (—R'SSR, —RSSR), sulfide (—R'SR, —RSR), diselenide (—R'Se—SeR), selenide (—R'SeR, —RSeR), thiol (—SH), nitrile (—CN), isonitrile, nitro (—NO$_2$), selenol (—SeH), trivalent phosphorous compounds, isothiocyanate, xanthate, thiocarbamate, phosphine, thioacid or dithioacid, carboxylic acids, hydroxylic acids, and hydroxamic acids.

R and R' are hydrocarbon chains which may optionally be interrupted by hetero atoms and which are preferably non-branched for the sake of optimum dense packing. At room temperature, R is greater than or equal to seven carbon atoms in length, in order to overcome natural randomizing of the self-assembling monolayer. At colder temperatures, R may be shorter. In a preferred embodiment, R is —(CH$_2$)$_n$— where n is between 10 and 12, inclusive. The carbon chain may optionally be perfluorinated. See Regen, S. L., et al., (1986), J. Am. Chem. Soc., vol. 108, pp. 6094–5, and Ringsdorf, H., et al., Angew. Chem. Int. Ed., Engl., vol. 27, pp. 113–158 (1988), both incorporated herein by reference.

Y may also have any surface property of interest. For example, Y could be any among the great number of groups used for immobilization in liquid chromatography techniques, such as hydroxy, carboxyl, amino, aldehyde, hydrazide, carbonyl, epoxy, or vinyl groups. Examples of sensing layer materials are set forth in "Patterning Self-Assembled Monolayers Using Microcontact Printing: A New Technology for Biosensors?," by Milan Mrksich and George M. Whitesides, published in TIBTECH, June, 1995 (Vol. 13), pp. 228–235; and U.S. Pat. No. 5,436,161 to J. Bergstrom, et al., hereby incorporated by reference.

In one embodiment of the invention, the gel is coupled to Y. For example, both the gel and the SAM may be hydrophilic.

Self-assembling monolayers of alkyl phosphonic, hydroxamic, and carboxylic acids may also be useful for the methods and compositions of the present invention. Since alkanethiols do not adsorb to the surfaces of many metal oxides, carboxylic acids, phosphonic acids, and hydroxamic acids may be preferred for X for those metal oxides. See J. P. Folkers, G. M. Whitesides, et al., Langmuir, 1995, vol. 11, pp. 813–824.

R may also be of the form (CH$_2$)$_a$—Z—(CH$_2$)$_b$, where $a \geq 0$, $b \geq 7$, and Z is any chemical functionality or compound of interest, such as sulfones, urea, lactam, etc.

The stamp may be applied in air, or under a fluid such as water to prevent excess diffusion of the alkanethiol. For large-scale or continuous printing processes, it is most desirable to print in air, since shorter contact times are desirable for those processes.

In one embodiment of the present invention, the pattern is formed on the metallized thermoplastic polymer with the self-assembling monolayer. In another embodiment of the present invention, the relief of the pattern is formed with the self-assembling monolayer. After the stamping process, the metallized areas on the plastic may optionally be passivated, for example, with a methyl-terminated self-assembling monolayer such as hexadecylmercaptan.

The appearance, or disappearance, of a holographic image can be used to indicate the presence of a stimulus in the local environment, thus, holograms can be used to simplify such a device and to present the display information to a consumer in a user-friendly fashion. A computer algorithm is used to calculate and generate diffraction hologram patterns of pre-defined objects.. Transfer of the computer-generated pattern to a responsive gel on metallized MYLAR® was accomplished via a simple printing process.

Applications for optical holography include digital data storage, microscopy, spectroscopy pattern recognition, and displays. Handbook of Optical Holography, H. J. Caulfield, editor (New York Academic Press 1979), incorporated herein by reference. Many of these applications rely on traditional holographic methods which are not well suited to the requirements of a sensor device.

The present invention allows one to computer-generate a complex holographic pattern of a specified object, print it on high resolution film, and convert the patterned elastomeric stamp for final transfer to a substrate upon which a selectively responsive material can be self-assembled to form the light-diffracting hologram pixels.

The ability to easily view a holographic image with the unaided eye involves consideration of a number of variables including (1) lighting conditions, (2) the refractive index modulation amplitude in the holographic material, (3) the hologram information content, (4) the type of hologram (volume phase, amplitude, transmission, reflection, etc.), (5) the thickness of the active diffraction layer, and (6) the hologram's activated pixel population. The use of a hologram for a sensor application requires precise receptor patterning, micro-reactor site activation by the stimulant, and a corresponding local change in light absorption or refractive index.

In the present invention, sensor information extracted from the light pattern diffracting from a regular array of micro-bumps is quantified and related to physical changes (size, shape, and refractive index) at the micro-bump level.

According to the present invention, the hologram pattern is fabricated for sensor applications. The method according to the present invention is compatible with continuous-print processes and it involves the following steps: (a) computation of the printed hologram pattern based on a preselected visual image to display, (b) formatting and printing the pattern on high-resolution transparency film, (c) photolithographic conversion of the pattern from gray-scale to surface-relief, (d) conversion of the surface-relief pattern to an elastomeric stamp, (e) stamp printing hydrophilic/hydrophobic mono-layer regions on a metallized MYLAR® substrate, and finally, (f) assembling analyte-responsive material on regions defined in the stamp printing process.

A special light source, such as a laser pointer or a white-light point source, is desirable for viewing the printed holographic image. Each location in the printed hologram contains information about a perspective view of the whole image. Therefore, when a laser pointer is used to project the image onto a screen, the beam only needs to propagate through a small section of the hologram to reconstruct the whole image. Alignment is not critical.

According to the present invention, a hologram pattern printed on a two-dimensional (surface) substrate represents only the real part of the complex light propagation information. Therefore, both a real and a symmetric conjugate (virtual) image are reconstructed during viewing. The "dual" image formation lends an added degree of flexibility but it also effectively reduces the unobscured, viewable image space by half.

The size, relative position, and information content of the holographic image are all limited by the resolution capabilities of the printer. A 3600 dot per inch (dpi) printout limits the image full fan angle to just over 5 degrees (the farther away from the film, the larger the image can be). Furthermore, to avoid overlap with the twin image, the effective image fan angle for a hologram generated with a maximum 3600 dpi resolution is reduced to 2.5 degrees. Methods exist whereby a 10 times photolithographic reduction of the hologram pattern can be used to increase the effective density of the pixels to 36,000 dpi, thereby, increasing the effective (unobscured) image fan angle to 32 degrees. If higher resolution is necessary conventional photo or electron beam lithographic processes can be used.

The diffracted image can be optimized for the specific method of indication. For example, an image as simple as a single, off-axis, projected dot may be ideal when using a photo-diode for detection, but a complex symbol image such as a skull and crossbones may be better suited for detection by the human eye. Each type of image can be specified; however, the hologram computation time increases linearly with each added image pixel.

Figure 10:
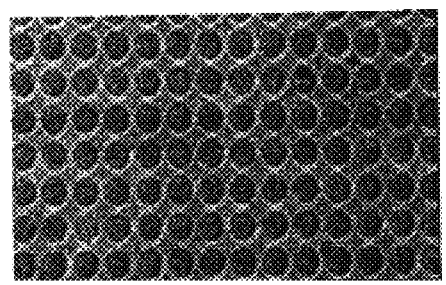
FIG. 10 is an illustration of a micro-bump array, as described in Example 7, where the bump center to center spacing is 15 microns.

A diffraction based sensor according to the present invention utilizes the interaction of light with a sensing medium to alter the transmitted or reflected diffraction pattern. FIG. 10 shows a periodic structure consisting of polymer micro-bumps patterned in an array. A change in the array's micro-bump size, shape, color, optical density, or refractive index may be triggered by the presence of some particular analyte in the local environment. Understanding the relationship between this physical change and the ensuing light diffraction change is important in the design of the present invention.

Figure 11:
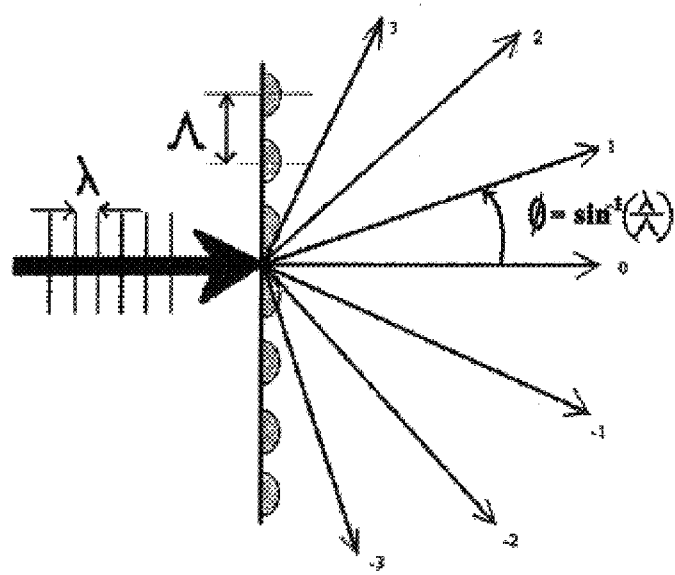
FIG. 11 is an illustration of a side view of a typical micro-bump array, as described below and in Example 7, showing that the diffraction angle $\phi$ and the number of visible diffraction orders are dependent on the incident wavelength $\lambda$, and the bump center-to-center spacing $\Lambda$.

A side-view of the array and the resulting (forward) diffraction orders is depicted in FIG. 11. Lower case lambda ($\lambda$) is the wavelength of the incoming light, and upper case lambda ($\Lambda$) represents the bump center to center spacing. Incident monochromatic light with wavelength $\lambda$ is diffracted into several orders with each particular order m characterized by the diffraction angle phi (sub m) equals arcsin (lamda×m)/$\Lambda$, for m equals 0, ±1, ±2, . . . , ±$\Lambda$/$\lambda$.

As can be concluded from FIG. 11, no sensing information is obtained by tracking the angle of diffraction; however, changes in the bump size and shape will be reflected in the relative intensities of the diffraction orders. A change in bump spacing, however, will change the diffraction angle.

Figure 12:
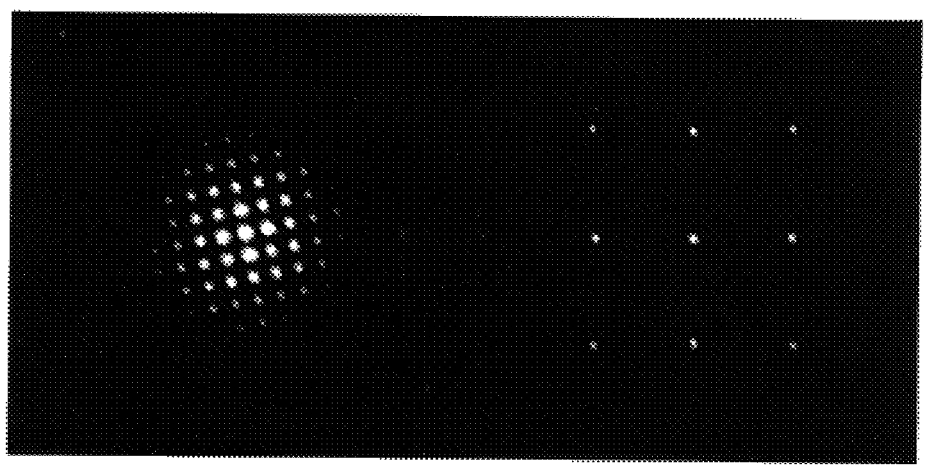
FIG. 12 illustrates a typical far field diffraction pattern, as described below, for micro-bump array with a 15 micron period (left-hand side) and for one with a 3 micron period (right-hand side).
Figure 13:
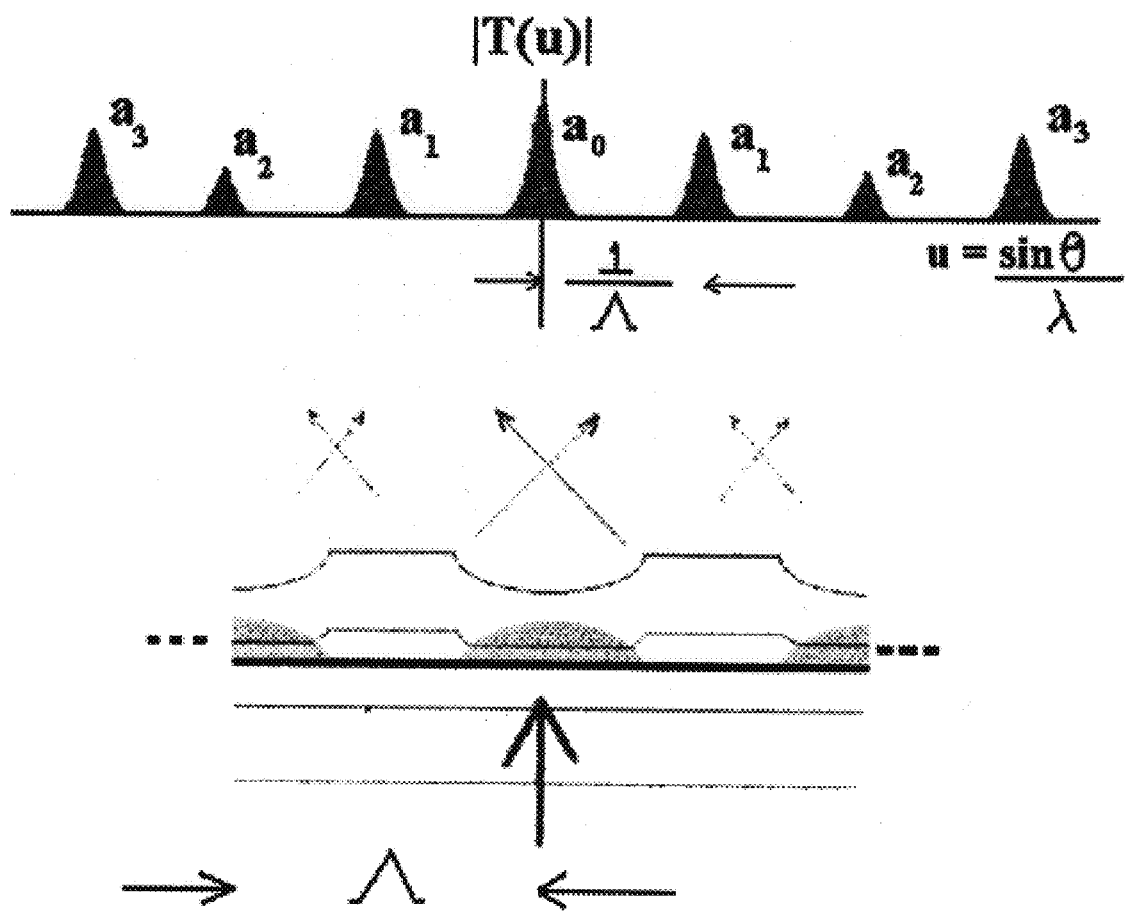
FIG. 13, as described below, graphically illustrates the transmitted far field electric field magnitude $|T(u)|$ as periodic, because the light wave front is periodically perturbed (delayed) as it travels through the higher refractive index micro-bumps, where each order's electric field ($a_0, a_1, a_2, \ldots$) is related to the perturbed wave front's Fourier series coefficient.

The far-field diffraction pattern for a typical micro-bump array is shown in FIG. 12. The left-hand side of FIG. 12 gives a diffraction pattern for a micro-bump array with a 15 micron period, and one for a 3 micron period on the right. The brightness or irradiance of each spot is related to the statistical average physical shape, size, and refractive index of the sampled bumps. The sampled bumps include all bumps illuminated by the probe beam. The spot irradiance and the bump profile are mathematically related by the Fourier coefficients of the near field transmitted beam series expansion expression. FIG. 13 graphically illustrates this relationship. The transmitted far field electric field magnitude |T(u)| is periodic, because the light wave front is periodically perturbed (delayed) as it travels through the higher refractive index micro-bumps, where each order's electric field ($a_0, a_1, a_2, \ldots$) is related to the perturbed wave front's Fourier series coefficient. Wave-fronts traveling through the bumps undergo a phase delay in proportion to the path-length traveled through the bump. The periodic phase-delay perturbation gives rise to a periodic far-field pattern. The far-field electric field magnitude of the diffraction pattern spots are related to the bump profile, h(x), through the near-field transmitted electric field, t(x)=exp(j kh(x)), where k=2 pi n/$\lambda$, where n is the refractive index of the bump region. The Fourier coefficients, and hence the square root of the detected irradiance for each order are calculated by the overlap integral: a (sub m)=(1/$\Lambda$) R, where R is the quantity t(x)cos(mkx) integrated from $-\Lambda/2$ up to $+\Lambda/2$, where it is assumed that t(x) is a symmetric function. If t(x) is not symmetric, one must also calculate the overlap integral of t(x) with the odd function, sin(mkx). This Fourier series coefficient expression is what allows us to predict and relate a change in the micro-bump array diffraction pattern to a change in the bump characteristics, which in turn are related to the local analyte concentration.

Figure 14:
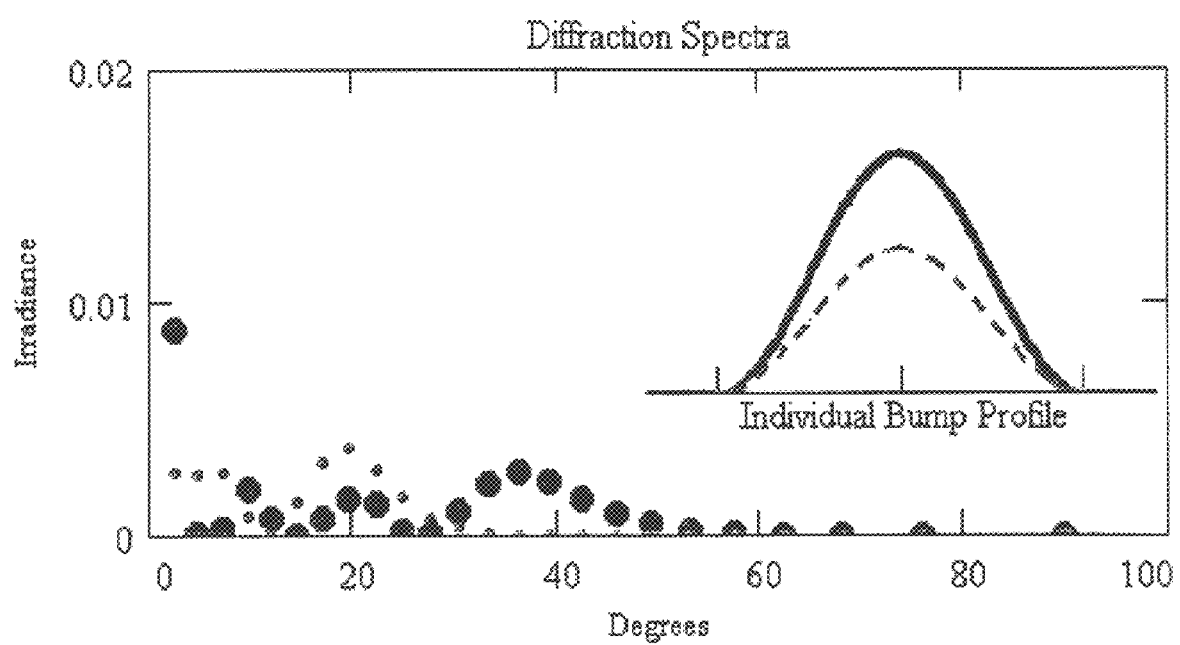
FIG. 14, as described below, illustrates a calculated half-plane, on-axis diffraction pattern irradiance for two different micro-bump arrays with refractive index=1.5, period $\Lambda$=15 micrometers, bump width=10 micrometers, bump height= 1.5 micrometers (large dots), bump height=0.9 micrometers (small dots). The abscissa is in degrees, and the ordinate is measured in power % of total transmittal of irradiance.

An example calculation depicting the diffraction order irradiance for two truncated cosinusoidal functions of different height is shown in FIG. 14. This figure illustrates a calculated half-plane, on-axis diffraction pattern irradiance for two different micro-bump arrays with refractive index= 1.5, period $\Lambda$=15 micrometers, bump width=10 micrometers, bump height=1.5 micrometers (large dots), bump height=0.9 micrometers (small dots). The abscissa is in degrees, and the ordinate is measured in power % of total transmittal of irradiance. An individual bump profile is shown in the inset. The example diffraction spectra shown in FIG. 14 illustrates a unique and measurable relationship between the bump shape and the diffraction pattern irradiance. Thus, an analyte-induced change in the bump profile would give rise to an intensity change in one or more diffraction orders. This intensity change can be measured, and in turn, related to the presence of analyte in the local environment.

The principal drawback associated with the micro-bump array diffraction sensor is the difficulty in relating and quantifying the changes in the detected diffraction irradiance signal to an input stimulus (i.e., temperature, pH, etc.). Small errors introduced at any point in the transformation from detected irradiance to temperature scale are greatly multiplied due to the non-linear transformations. Sensitivity for such a device is highly dependent on the bump geometry and initial volume. Furthermore, since the gel has a minimum trigger temperature and since it undergoes an approximate 10 times volume change over a few degrees, the dynamic range of the sensing device of the present invention is extremely limited.

One of the goals established from the onset was that the detection results should be easily interpreted without the aid of support electronics. Therefore, it is necessary to assemble the micro-bump reactors in a pattern such that the diffracted light forms an image that is easily recognizable by the eye. Furthermore, a salient feature of the diffracted image should change to indicate detection of a pre-selected analyte in the local environment.

The present invention is a unique combination of microlithographic and SAM fabrication techniques that have made it possible to transform the gray-scale film printout to a surface-relief pattern in photoresist, form a stamp of the pattern, and define responsive-gel-adhering, hydrophilic-patterned regions on metallized MYLAR®. The type of hologram sensor platform produced according to the present invention is unique with a whole set of unique properties that may be advantageous when compared side by side with other types of sensors. The integration of the visual display with the sensing surface according to the present invention is an important step in reducing costs associated with support electronics.

This invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

Example 1

Printing of nickel/gold-coated MYLAR® (polyethylene terephthalate) with patterns of 16-mercaptohexadecanoic acid and hexadecanethiol A nickel/gold alloy of 15.9 nM thickness was sputter-coated onto 7 mil MYLAR®. The composition had 65% visible light transmittance, and 65 ohms/$cm^2$ resistance. The following results from XPS surface analysis were obtained.

| Sputter Time (sec) | % C | % O | % Au | % Ni |
|---|---|---|---|---|
| 0 | 51.5 | 8.0 | 40.5 | ND |
| 15 | 33.3 | 6.4 | 60.3 | ND |
| 30 | 20.2 | ND | 71.7 | 8.0 |
| 60 | 19.3 | ND | 72.4 | 8.3 |

ND means "not detected", i.e., less than 0.2 atompercent.

These results show that the outermost surface of the Ni/Au alloy is predominantly Au, i.e., Ni is not detected until after approximately 5.0 nM of Au is removed. Thus, the alloy presents a surface that resembles pure gold and can be used as a "pure gold" surface for contact printing.

Figure 2:
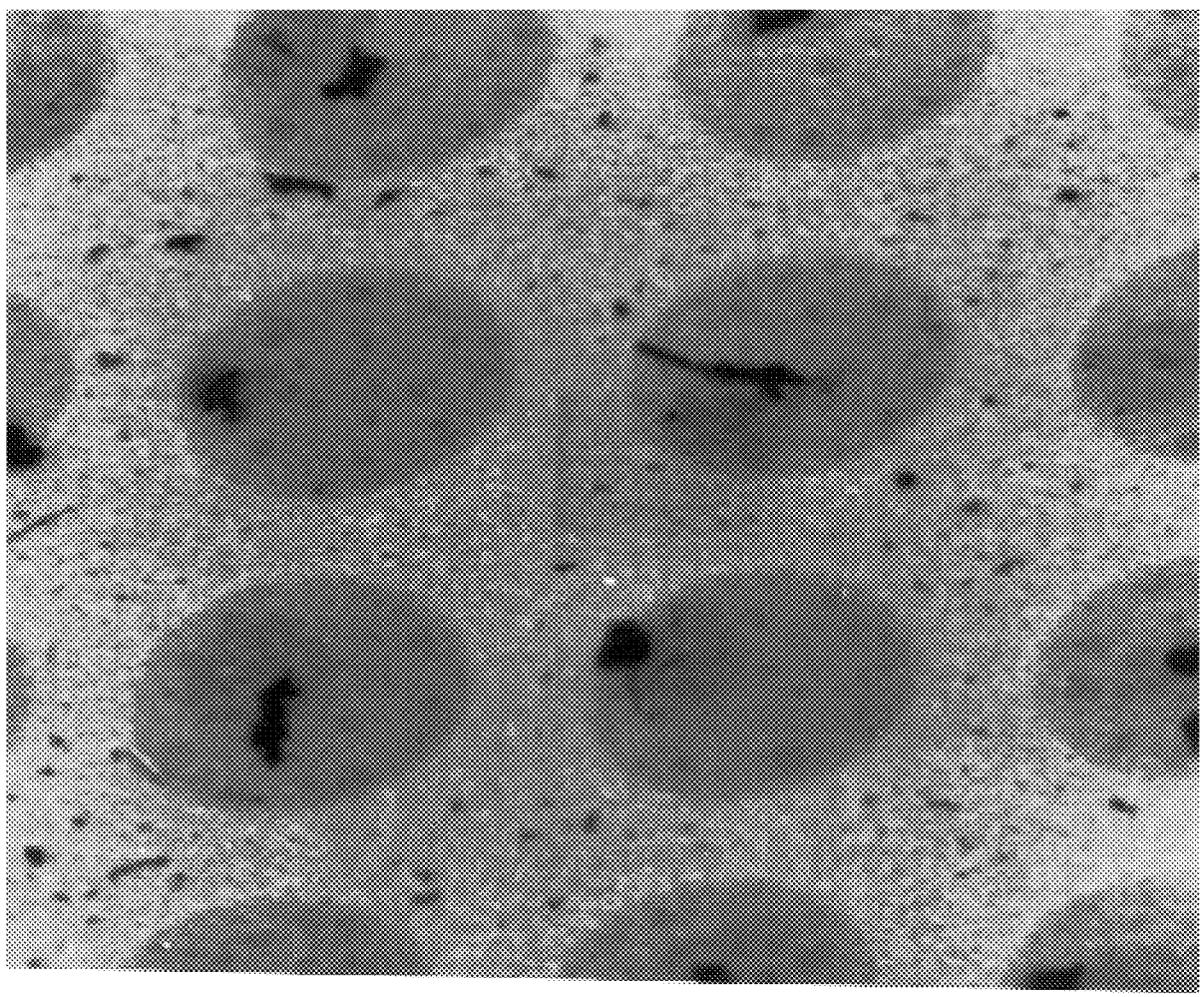
FIG. 2 is a field emission secondary electron microscope image of 10 micron-diameter circles of hydrophilic self-assembling monolayers formed by printing of 16-mercaptohexadecanoic acid onto MYLAR® metallized with Ni/Au alloy, as described in Example 1.

MYLAR® film modified with a sputter-deposited nickel/alloy topcoat was obtained from Courtaulds Performance Films (21034 Osborne Street, Canoga Park, Calif. 91304). Patterns of hydrophilic, carboxy-terminated alkane thiols were stamped onto the Ni/Au metallized MYLAR® using $CH_3(CH_2)_{15}SH$ and $HOC(O)(CH_2)_{15}SH$ acid by the following method. (See FIG. 1). An exposed and developed photoresist pattern of 10 micron diameter circles on a silicon wafer was used as the master. Polydimethylsiloxane (PDMS;

silicone elastomer 184; Dow Corning Co., Midland, Mich.), was polymerized on a master to produce a stamp with ten micron-diameter circles spaced five microns apart. The stamp was inked by exposure to a solution (1 to 10 mM in ethanol) of 16-mercaptohexadecanoic acid, and allowed to air-dry. The substrate was contacted with the stamp for 50 seconds and washed for 2 to 4 seconds with a solution of hexadecanethiol (1 to 10 mM in ethanol) which reacts with the gold in regions not covered by the carboxy terminated thiol. A patterned surface with $CO_2H$ and $CH_3$ is thus produced. The substrate was finally washed for 10 seconds in ethanol and dried in a stream of nitrogen. The results of this printing are shown in FIG. 2.

Figure 3A:
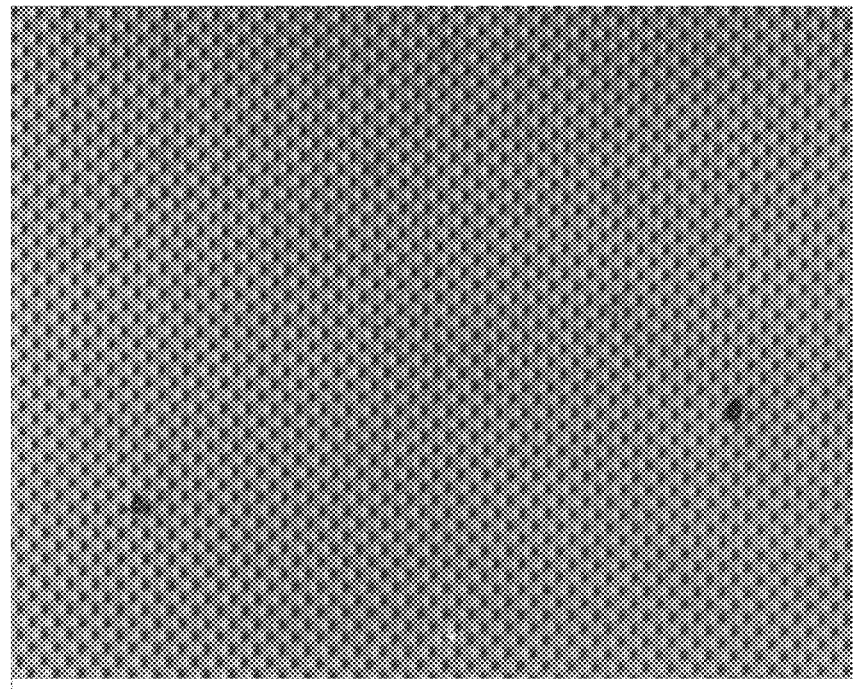
FIG. 3a is an optical photomicrograph at 300× magnification of 10 micron-diameter circles with center to center spacing of 15 microns of hydrophilic self-assembling monolayers formed by printing of 16-mercaptohexadecanoic acid, as described in Example 1, below, and after exposure to a high surface energy, curable, optical adhesive. The adhesive is cured by ultraviolet light (UV) exposure.

These hydrophilic self-assembling monolayer circles allow for selective placement of high surface tension fluids such as water, triethylene glycol, or ultraviolet light curable urethane acrylic adhesives. Aqueous solutions of responsive gels with or without indicators sensitive to analytes can also be placed selectively on the monolayer circles. These liquids can contain dissolved and suspended reagents that react chemically or physically with targeted analytes, thus making the coated plastic film a collection of 10 micron microreactors suitable for low-cost, disposable chemical sensors. An example of such a device is shown in FIG. 3a.

Figure 3B:
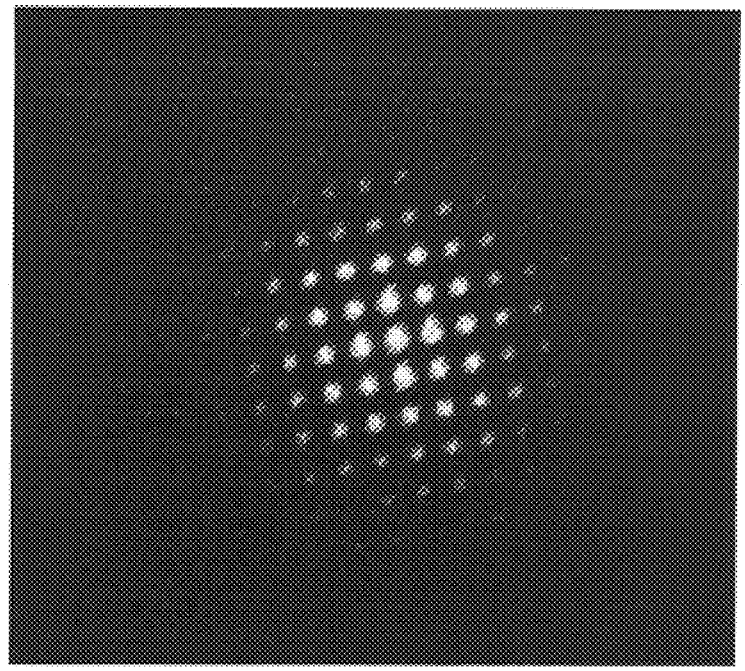

Diffraction of visible light was shown with these compositions. Both reflected and transmitted diffraction patterns were observed when using 5 mW, 670 nM laser illumination. FIG. 3b is a photograph of the diffraction pattern formed by visible light shown through the self-assembling monolayer pattern of FIG. 3a. Rainbow diffraction colors were observed with transmitted white light.

Measurement of Contact Angles

Contact angles were measured on a Rame-Hart Model 100 goniometer at room temperature and ambient humidity. Water for contact angles was deionized and distilled in a glass and Teflon apparatus. Advancing and receding contact angles were measured on both sides of at least three drops of each liquid per slide; data in the figures represents the average of these measurements. The following method was used for measuring contact angles: A drop approximately 1–2 microliters in volume was grown on the end of a pipette tip (Micro-Electrapette syringe; Matrix Technologies; Lowell, Mass.). The tip was then lowered to the surface until the drop came in contact with the surface. The drop was advanced by slowly increasing the volume of the drop (rate approximately 1 microliter/second). Advancing contact angles of water were measured immediately after the front of the drop had smoothly moved a short distance across the surface. Receding angles were taken after the drop had smoothly retreated across the surface by decreasing the volume of the drop.

X-ray Photoelectron Spectroscopy (XPS)

X-ray photoelectron spectra were collected on a Surface Science SSX-100 spectrometer using a monochromatized Al K-alpha source (hv=1486.6 electron volts). The spectra were recorded using a spot size of 600 micrometers and a pass energy on the detector of 50 electron volts (acquisition time for one scan was approximately 1.5 minutes). For the monolayers, spectra were collected for carbon and oxygen using the Is peaks at 285 and 530 eV, respectively; the binding energies for elements in the monolayer were referenced to the peak due to hydrocarbon in the C 1s region, for which the binding energy was fixed at 284.6 eV. Spectra for the solid hydroxamic acid were collected using an electron flood gun of 4.5 eV to dissipate charge in the sample. The binding energies for the substrates were not standardized to a reference sample. All spectra were fitted using an 80% Gaussian/20% Lorentzian peak shape and a Shirley background subtraction. See J. P. Folkers, G. M. Whitesides, et al., *Langmuir*, vol. 11, no. 3, pp. 813–824 (1995).

Condensation Figures

Condensation figures (CFs) are arrays of liquid drops that form upon condensation of vapor onto high surface energy regions of a patterned solid surface. The examination of condensation figures has historically been used as a method to characterize the degree of contamination on an otherwise homogeneous surface. One is able to impose a pattern on arrays of condensed drops by patterning the surface underlying them into regions of different solid-vapor interfacial free energy and to characterize the patterned CFs by photomicroscopy and optical diffraction. It can be demonstrated that appropriately patterned CFs can be used as optical diffraction gratings and that examination of the diffraction patterns provides both a rapid, nondestructive method for characterizing patterned self-assembling monolayers and an approach to sensing the environment (see FIG. 6, explained below). Because the form of the CFs—that is, the size, density, and distribution of the drops is sensitive to environmental factors, CFs of appropriate size and pattern diffract light and can be used as sensors. This principle is demonstrated by correlating the temperature of a substrate patterned into hydrophobic and hydrophilic regions, in an atmosphere of constant relative humidity, with the intensity of light diffracted from CFs on these regions.

Appropriate patterns are formed from self-assembled monolayers (self-assembling monolayers) on gold/nickel by using combinations of hexadecanethiol [$CH_3(CH_2)_{15}SH$], 16-mercaptohexadecanoic acid [$HS(CH_2)_{15}COOH$], and 11-mercaptoundecanol [$HS(CH)_{11}OH$]. Several techniques are now available for preparing patterns of two or more self-assembling monolayers having 0.1- to 10-$\mu$m dimensions.

At 20° C., an incident beam of light from a laser (helium-neon laser, wavelength=632.8 nm) produced a single transmitted spot because no water had condensed on the surface, and the transmittance of the regions covered with different self-assembling monolayers were effectively indistinguishable. As the surface was exposed to warm, moist air, droplets of water condensed preferentially on the hydrophilic regions. Diffraction patterns appeared in the light transmitted from the surface. Under these conditions, light was transmitted coherently from the regions where no water had condensed and was scattered by the regions where water had condensed. The condensation figures disappeared within several seconds as the water droplets which condensed on the self-assembling monolayers evaporated.

The ability to form condensation figures can be ascertained by the relative contact angles of water on the hydrophobic and hydrophilic self-assembling monolayers. Unpatterned monolayers of the appropriate thiol were prepared by immersion of the substrate in a dilute solution for one hour, followed by rinsing with ethanol and air drying.

The contact angles of water on Au(Ni)/MyLAR® reacted with $CH_3(CH_2)_{15}SH$ and $HOC(O)(CH_2)_{15}SH$ were 100° and 62$^\alpha$, respectively. The untreated Au(Ni)/MYLAR® contact angle for water was 73–77°. This water contact angle is similar to that obtained for Au coated $SiO_x$ wafers, which is 73–74° (data not shown).

Condensation Figures [*Science*, Vol. 263, 60 (1994), incorporated herein by reference] with equivalent optical diffraction can be formed on Au/Ni:MYLAR®, relative to known art with Au:SiOx. The chemistry of alkane-thiols reacting with Au/Ni:MYLAR® is similar to that reported in the literature for Au:SiOx.

A field emission secondary electron microscope image of 10 micron-diameter circles of hydrophilic self-assembling monolayers formed by printing of 16-mercaptohexadecanoic acid onto MYLAR® metallized with Ni/Au alloy is shown in FIG. 2. FIG. 3a is an optical photomicrograph at 300×magnification of 10 micron-diameter circles of hydrophilic self-assembling monolayers formed by printing of 16-mercaptohexadecanoic acid, and after exposure to a high surface energy, curable, optical adhesive. The adhesive was cured by ultraviolet light (UV) exposure.

FIG. 3b is a photograph of the diffraction pattern formed by visible light shown through the self-assembling monolayer pattern described by FIG. 3a.

Figure 4:
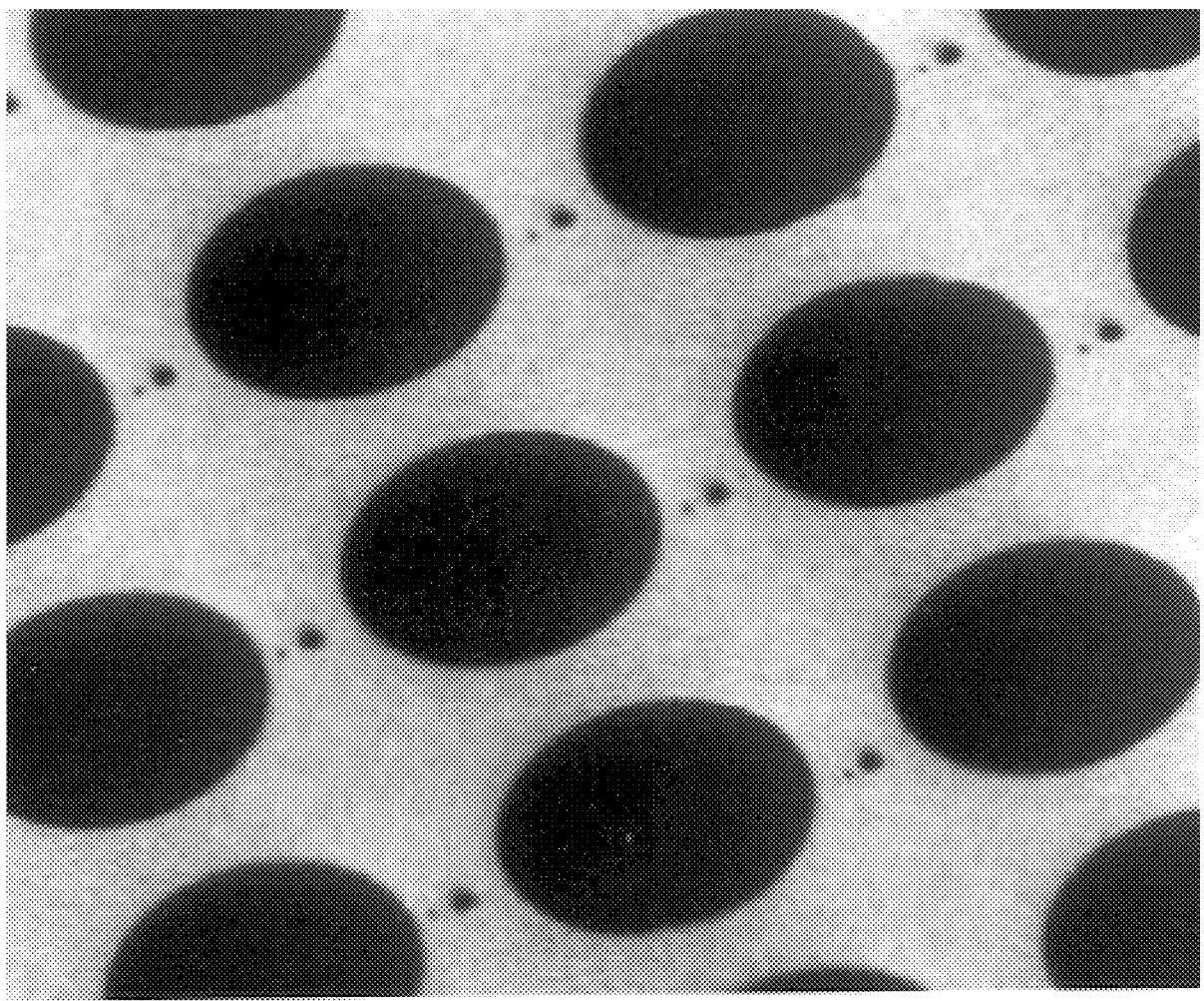
FIG. 4 is a field emission secondary electron micrograph image of 10 micron-diameter circles formed of self-assembled photocurable polymers on hydrophilic self-assembling monolayers, printed as described in Example 1.

FIG. 4 is a field emission secondary electron micrograph images of 10 micron-diameter circles formed of self-assembled photocurable polymers on hydrophilic self-assembling monolayers.

Figure 6:
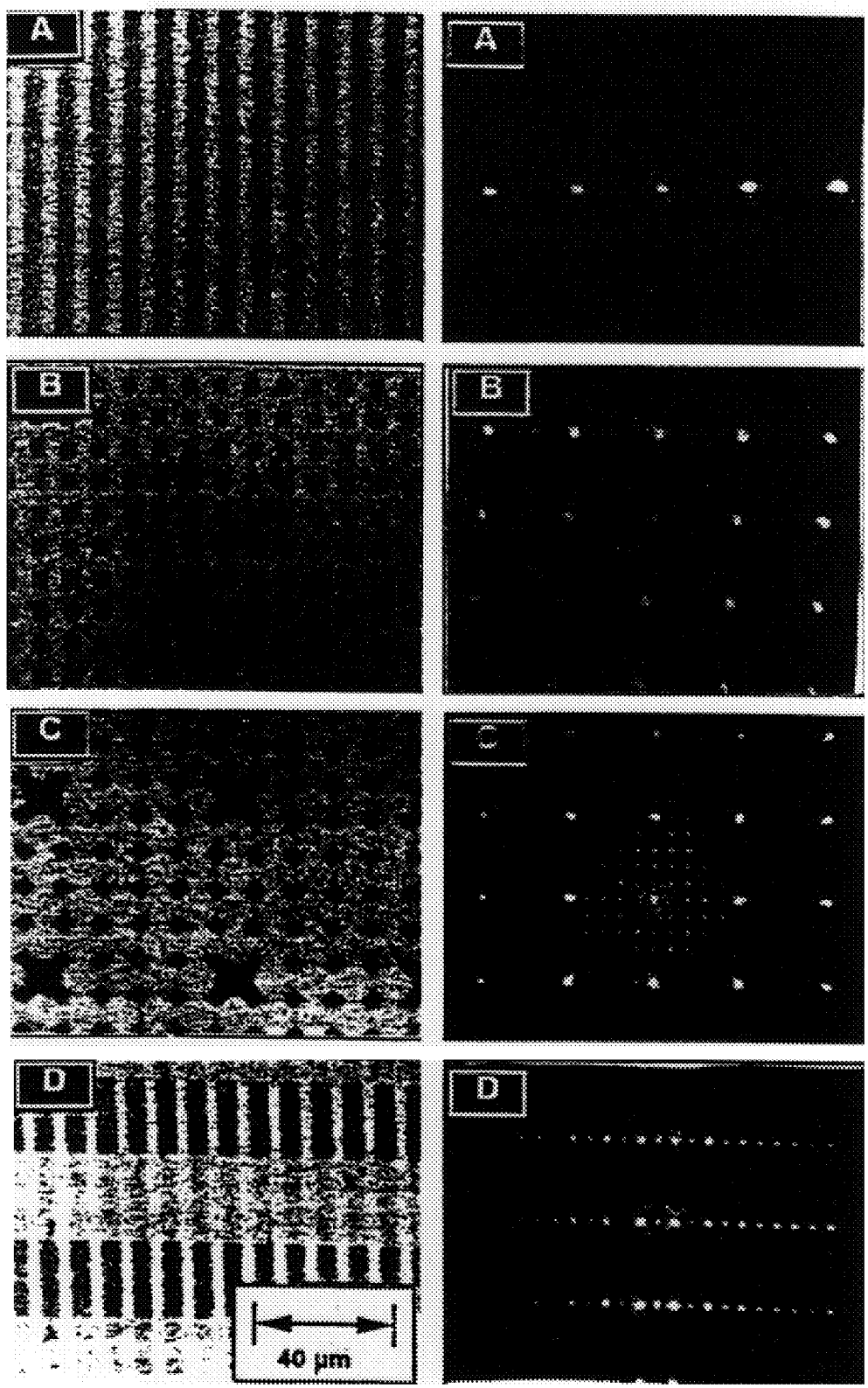
FIG. 6, in the left hand vertical column shows printed arrays, on in the right-hand column shows the resulting diffraction patterns.

FIG. 6, in the left hand vertical column, shows printed arrays, on the right-hand column shows the resulting diffraction patterns. The inset in the left hand column in FIG. 6 D gives the scale of the patterns.

Example 2
Placing a hydrogel atop patterns of self-assembling monolayers printed on nickel/gold-coated MYLAR® (polyethylene terephthalate)

Solutions of a chemically responsive gel were prepared by polymerizing an aqueous solution of N-isopropylacrylamide (NIPA) (18 weight %) using persulfate and ascorbic acid. Briefly, a 250 mL Erlenmeyer flask was charged with 18.0 gm NIPA monomer and 80 g distilled water. The resulting solution was stirred using a magnetic stir bar, and 0.08 g potassium persulfate was allowed to dissolve. A rubber septa was placed on the flask, and inlet and outlet needles were used to purge the flask with nitrogen. Stirring constantly, the flask was cooled in an ice bath to approximately 0° C. A solution of 0.07 g L-ascorbic acid in 3 mL distilled water was injected into the mixture. Within 2 hours, the mixture had polymerized to a very viscous, clear solution. The resulting polymer was diluted with additional water to a concentration of 2 percent by weight. To this solution was added an equal volume of toluene to produce a two phase system. The printed MYLAR® film of Example 1 was drawn through both phases of this system to self-assemble the aqueous solution of polymer onto the patterned, hydrophilic SAM. This resulted in a sensing device containing a stimuli responsive gel.

Example 3
Printing of gold-coated MYLAR® (polyethylene terephthalate) with patterns of 16-mercaptohexadecanoic acid and hexadecanethiol Patterns of gold-coated MYLAR® (polyethylene terephthalate) were printed with patterns of 16 mercaptohexadecanoic acid and hexadecanethiol, in a manner similar to that shown in FIG. 1, and described below.

Figure 5:
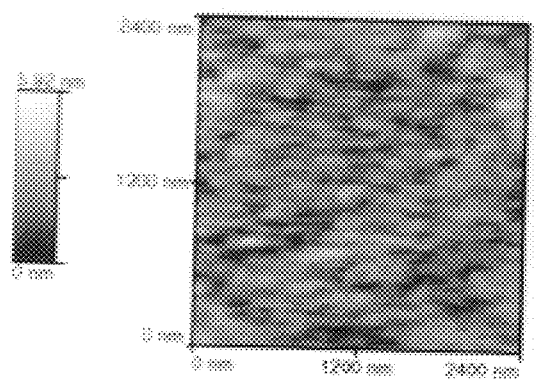
FIG. 5 is an atomic force microscopy image of evaporated gold on MYLAR®, purchased from Courtaulds Performance Films (Canoga Park, Calif.). The average roughness of the gold layer is 3–4 nanometers, with maximum roughness of 9 nanometers.
Figure 5:
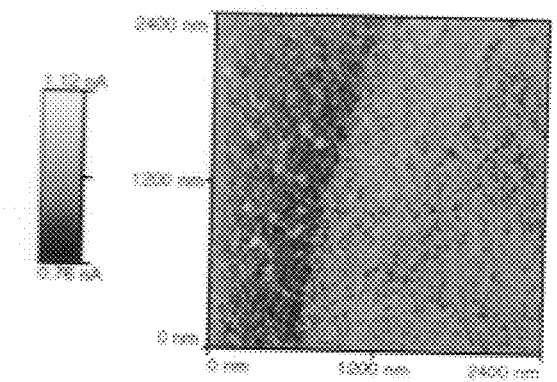
Figure 5:
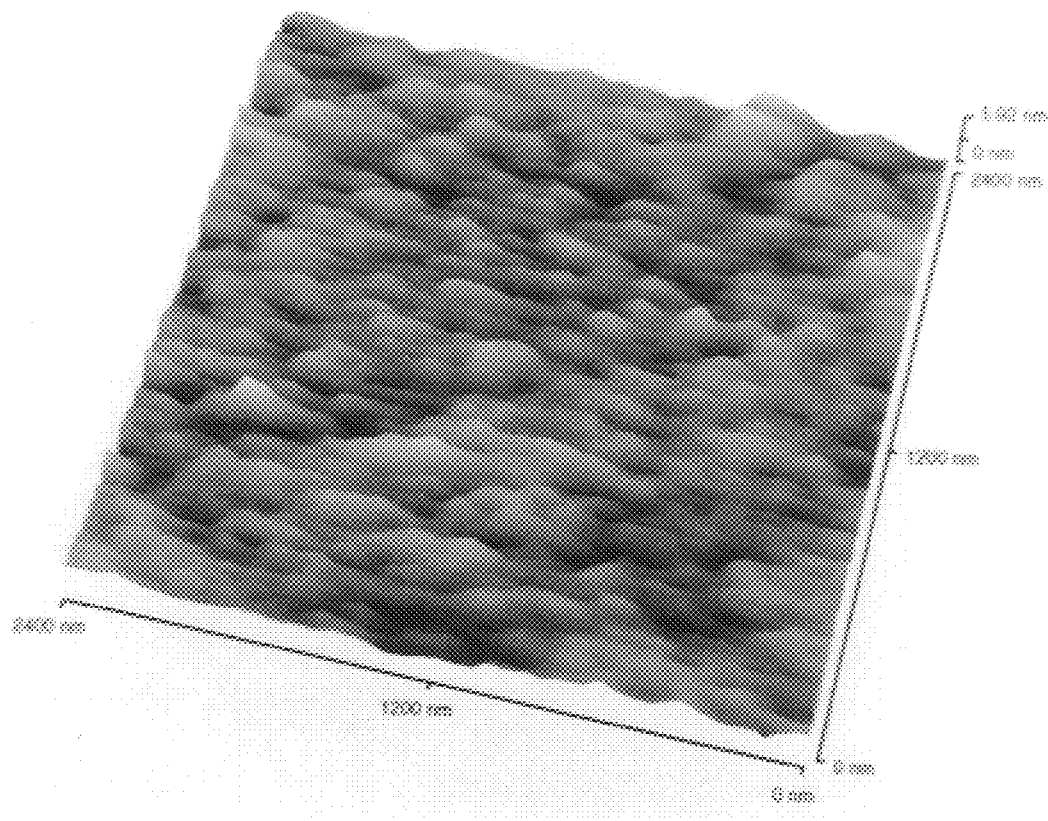

MYLAR® film modified with a plasma deposited gold topcoat was obtained from Courtaulds Performance Films (Canoga Park, Calif. 91304). An atomic force microscopy image of this MYLAR® film is shown in FIG. 5. Polymer film thickness between 2 and 7 mils and gold topcoats producing a surface resistance of 65 ohms per square centimeter with a visible light transmittance between 20% and 65% were used.

Patterns of hydrophilic, carboxy-terminated alkane thiols were stamped onto gold-coated film using 16-mercaptohexadecanoic acid by the following method. An exposed and developed photoresist pattern of 10 micron diameter circles on a silicon wafer was used as the master. Polydimethylsiloxane (PDMS; silicone elastomer 184; Dow Corning Co., Midland, Mich.), was polymerized on a master to produce a stamp with ten micron-diameter circles spaced five microns apart. The stamp was inked by exposure to a solution (1 to 10 mM in ethanol) of 16-mercaptohexadecanoic acid, and allowed to air-dry. The substrate was contacted with the stamp for 50 seconds and washed for 2 to 4 seconds with a solution of hexadecanethiol (1 to 10 mM in ethanol). The substrate was finally washed for 10 seconds in ethanol and dried in a stream of nitrogen. (Results not shown).

Example 4
Experimental Diffraction-measurement

Figure 15:
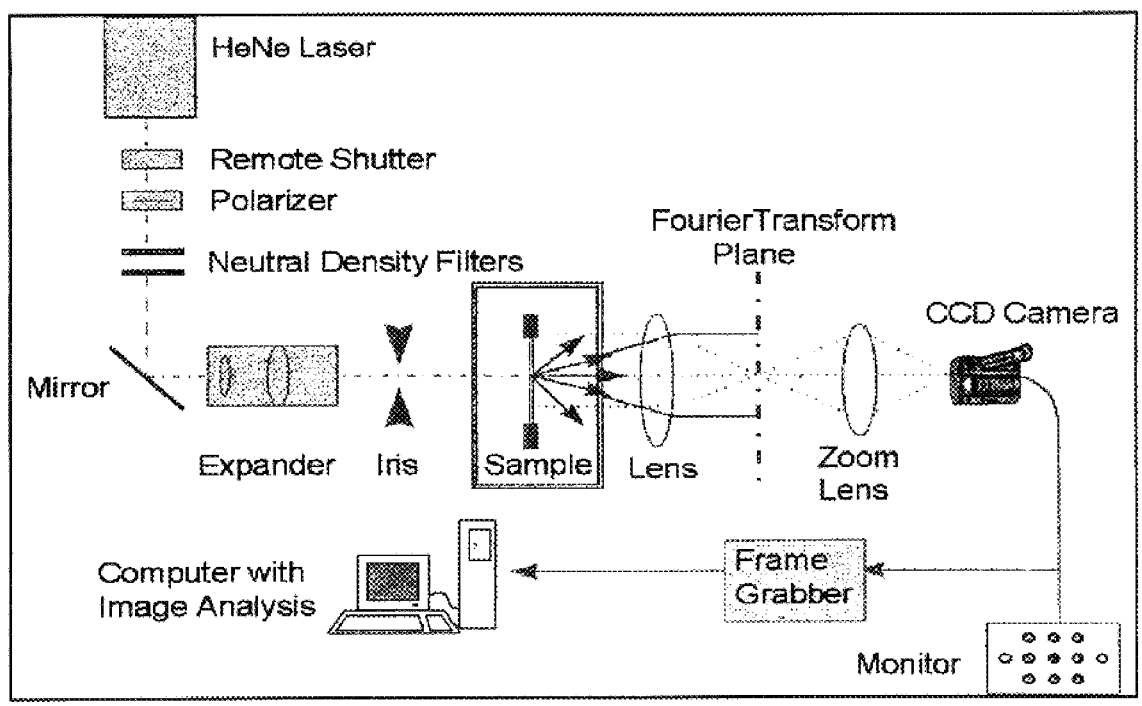
FIG. 15, as described in Example 4, illustrates an experimental setup for quantifying the diffraction spectra from a diffraction array.

An experimental diffraction-measurement schematic is shown in FIG. 15. This figure shows an experimental setup for quantifying the diffraction spectra from a diffraction array. The elements of the set-up include a Helium/Neon laser, a remote shutter, a polarizer, a neutral density filter, a mirror, and expander, an iris, a sample, a lens, a Fourier transformed lens, a zoom lens, a CCD camera, a monitor, a frame grabber, and a computer with image analysis software.

Figure 16:
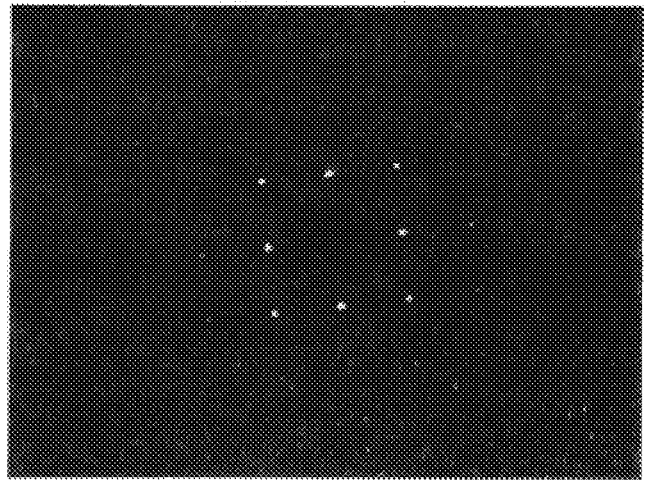
FIG. 16, as described in Example 4, illustrates a diffraction image from poly-N-isopropylacrylamide micro-bump sensor array, where the zero-order beam was blocked to eliminate CCD saturation.

Coherent light with wavelength $\lambda=0.6328$ micrometers was diffracted by the sample which was enclosed in an environment chamber. The diffraction orders were collected by a lens and imaged onto a CCD camera where the image was displayed on a monitor and stored on a computer for image processing and analysis. This experimental setup was used to measure the two dimensional diffraction image intensity from a self-assembled-monolayer (SAM)-patterned array of temperature-responsive poly-N-isopropylacrylamide (NIPA). The poly-NIPA bumps undergo a volume shrinkage with increasing temperature, therefore, the detected diffraction order irradiance from one spot to the next changed, as was predicted by the model, with a rise in temperature. An example image captured during this experiment is shown below in FIG. 16. The zero order beam in this figure was blocked to eliminate CCD saturation. S. Hirotsu, Y. Hirokawa, and T. Tanaka, "Volume-phase transitions of ionized N-isopropylacrylamide gels," *J. Chem. Phys.*, vol. 87, no. 2, pp. 1392–1394, Jul. 15, 1987, incorporated herein by reference.

Conversion from the diffraction pattern's gray-scale image to temperature scale must be done with extreme care because it involves at least five sequential transformations including: (1) a non-linear relationship between the gel temperature and the micro-bump volume, (2) a relationship between the bump volume and shape, (3) a non-linear (oscillating) relationship between the bump shape and the signal detected with the CCD device (see FIG. 17) and finally, (4) scaling and quantization of the detected signal for digital storage of the image.

Figure 17:
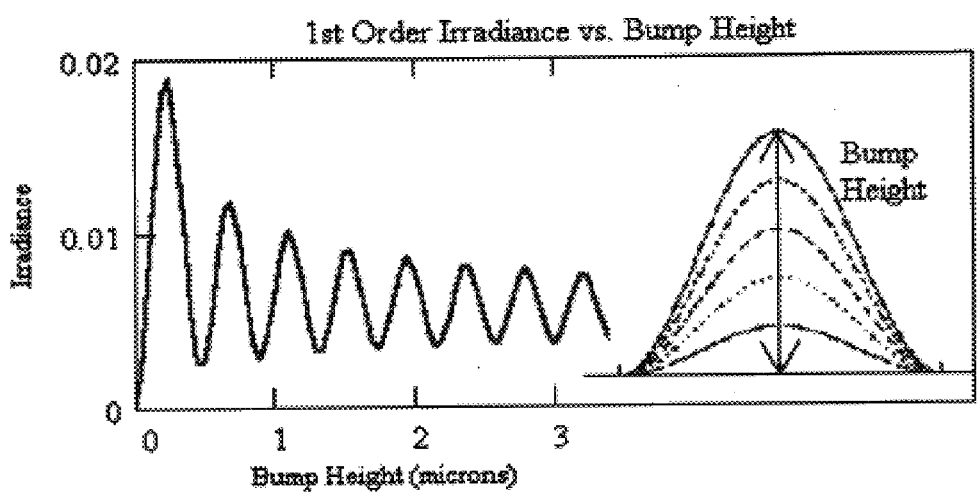
FIG. 17, as described in Example 4, is a graph of the first-order diffraction irradiance as a function of the micro-bump height for a bump refractive index of 1.5, base width of 10 micrometers, and a period of 15 micrometers. The oscillating irradiance curve limits the useful bump height to approximately 0.3 micrometers for this geometry. The abscissa measure bump height in microns, and the ordinate measures irradiance in power % of total transmittal of irradiance.

Assuming the bump is cosinusoidal shaped with height h, and constant base diameter d, the volume v, of the microbump is $v=hd^2(1-2/pi)$, i.e., the volume is linearly related to the height for this shape. FIG. 17 is a graph of the first-order diffraction irradiance as a function of the micro-bump height for a bump refractive index of 1.5, base width of 10 micrometers, and a period of 15 micrometers. The oscillating irradiance curve is linear in a finite range, and limits the useful bump height to approximately 0.3 micrometers for this geometry. The abscissa measure bump height in microns, and the ordinate measures irradiance in power % of total transmittal of irradiance.

Example 5
Holographic pattern design and method

A novel hologram synthesis method compatible with contact printing and SAM (see A. Kumar, H. A. Biebuyck, G. Whitesides, Langmuir, vol. 10, no. 5, pp. 1498–1511 (1994), incorporated herein by reference) technology was developed.

The hologram computation is based on traditional holography theory with adjustments made to account for physical considerations such as printer resolution, wavelength scaling, sampling theory, and image content. The recent development and availability of high-resolution film printers is one of key enabling technologies which has allowed rapid refinement cycles and cost effective hologram synthesis. It should be stressed that the diffracted image quality is directly limited by the printer resolution, i.e., by how small and close together individual dots can be placed in the printer output. A 3600 dot per inch specification means that the minimum resolution the printer is capable of producing is 7 micrometer diameter dots with a 7 micrometer center-to center spacing. To put this into perspective, standard holographic silver halide films range in grain size from 0.05 micrometers to 1.0 micrometers. The table below summarizes the "rule of thumb" resolution requirements for embossed holograms of various quality. One must be aware that the 7 micrometer feature-size is huge in terms of traditional display holography and severe limitations are imposed by such resolution, nevertheless, a limited class of special thin transmission holograms can be readily made with such resolution, enabling low-cost development and testing of the holographic diffraction sensor.

| "Rule of thumb" resolution requirements for embossed holograms of various quality | | |
|---|---|---|
| EMBOSSED IMAGE QUALITY | DENSITY (pixels/mm) | FEATURE SIZE (microns) |
| Very High Quality 3D images | 14,000 | <0.7 |
| Medium Quality 3D images | ~1,000 | ~1.0 |
| Good 2D, 3D images | ~600 | ~1.7 |
| Good 2D, Poor 3D images | <450 | >2.0 |

Figure 18:
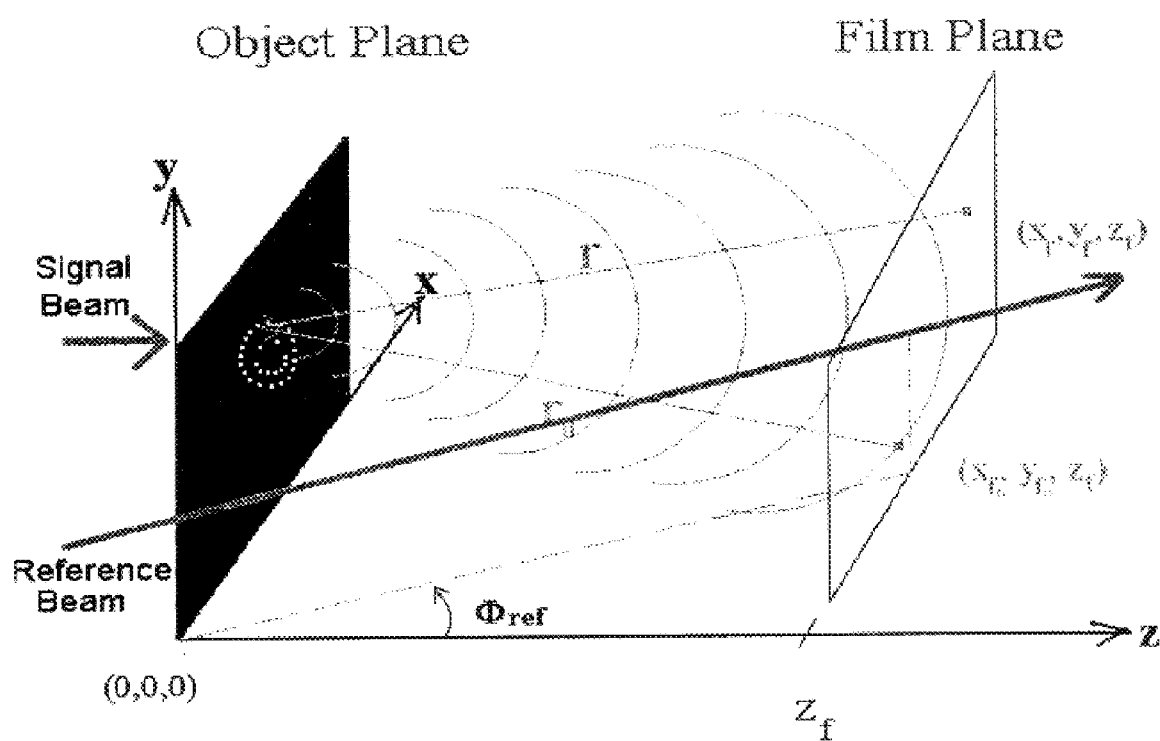
FIG. 18, as described in Example 5, illustrates a holographic recording setup, with an object plane, a film plane, a signal beam, and a reference beam, with a smiling face as the holographic image.

FIG. 18 depicts the geometry for a traditional holographic transparency recording setup. The figure shows an object plane, a film plane, a signal beam, and a reference beam, with a smiling face as the holographic image. Cartesian coordinates are also shown, with (0,0,0) as the reference point, and Phi as the angle the reference beam makes with the z axis in the x-z plane. The object plane consists of small transparent holes in an opaque background. The signal and reference beams are assumed mutually coherent and monochromatic. The light propagating from each point in the object plane can be expressed, using Huygen's principle, as an expanding spherical wave with an electric field phasor representation: $E(r)=\exp(jkr)/r$, where $k=2 pi/\lambda$ and $j=sqrt(-1)$. The reference plane-wave beam is incident on the film plane at an angle phi sub(ref) with respect to the film normal. The image beam and the reference beam interfere and the constructive/destructive interference pattern is recorded in the film. Setting phi sub(ref)=0 reduces the resolution requirements of the film but an on-axis hologram is produced. The drawbacks of the on-axis hologram will be discussed subsequently.

The holographic recording setup in FIG. 18 can be modeled on a computer and an interference pattern at the film plane can be calculated, converted to a gray-scale bit map image, and printed out on a high-resolution film printer. The result is a computer generated transparency hologram. Each of the N object points (i.e., the dots making up the smile-face image in FIG. 18) are expressed in Cartesian coordinates as $(x_0, y_0, z_0)$. Each point can be assigned a unique position, therefore, 3-dimensional object representation is allowed. Each point in the film plane is expressed as $(x_f, y_f, z_f)$ where $z_f$ is the minimum distance from the object to the film plane, and it is usually a fixed value, thereby denoting a flat piece of recording film. A convenient zero-phase reference point in the film plane is picked and designated $(x_{f0}, y_{f0}, z_{f0})$. The minimum distance from each point on the object to an arbitrary point on the film is:

$$r=[(x_0-x_f)^2+(y_0-y_f)^2+(z_0-z_f)^2]^{1/2}$$

The radial distance to the zero- phase reference point is:

$$r_0=[(x_0-x_{f0})^2+(y_0-y_{f0})^2+(z_0-z_{f0})^2]^{1/2}$$

The difference between the r and $r_0$, scaled by the propagation constant, k, gives the differential phase of the image wave for each point on the film plane. The main hologram synthesis equation is:

$$H(x_f, y_f)=\Sigma \exp [jk(r-r_0)-x \sin (\text{phi sub(ref)})]$$

summed from n=1 to N. The synthesis equation is used in calculating the contribution of each N points comprising the object and it is solved at each sample point $(x_f, y_f, z_f)$ in the film plane. If the film plane is to be represented by an M×M array of sample points, then the number of synthesis calculations required is N×M².

The synthesized hologram consists of a two-dimensional array of sample points representing the complex phase and amplitude of the interference pattern between object and reference beams. Conversion of the complex array values to a gray-scale must be done before printing the hologram pattern because only the amplitude information can be represented by the printer.

Since the imaginary part of the information is discarded in the conversion, it makes no sense to calculate it in the first place. Therefore, a more efficient and direct synthesis equation is:

$$H(x_f, y_f)=\Sigma \cos (jk[(r-r_0)-x \sin (\text{phi sub(ref)})]$$

where the summation is from n=1 to N. This synthesis equation can be implemented with a computer, for example, the MathCad program (MathSoft, Cambridge, Mass.).

Example 6
Sampling Requirements

Care must be taken to calculate enough points on the hologram interference pattern (i.e., to sample at a sufficiently high spatial frequency) so that the information is preserved and aliasing does not occur. A form of the Shannon or Nyquist sampling theorem can be applied to the case at hand. A. V. Oppenheim and R. W. Schafer, *Discrete time signal processing* (Prentice-Hall, Englewood Cliffs, N.J. 1989), incorporated by reference. However, a more direct and physically appealing method was devised to gain insight into the problem and to assist with the design.

Since the calculated hologram consists of periodic sample points which, upon printout, are separated by a minimum center-to-center spacing of Λ=7 micrometers (due to the resolution of the printer), the reconstructed image will also be repeated periodically in space with an angular repetition (recall FIG. 11) equal to:

$$\phi_m=\sin^{-1}(\lambda x/\Lambda)$$

which is approximately 5 degrees for red light incidence (λ=0.6328 micrometers). This means that the full image fan angle can not exceed 5 degrees without overlapping with the replicated images. Full use of the image plane is possible only when the printer resolution is equal to the incident wavelength, and when the all the complex phase information is retained. The limited printer resolution ultimately limits the extent of the image and specifies the minimum image projection distance from the film for a given image extent.

Example 7
Conjugate Beam Aberrations

Another consideration that plays an important role in the hologram design is the unwanted twin or conjugate beam that arises due to the inability to print all the phase information.

Figure 19:
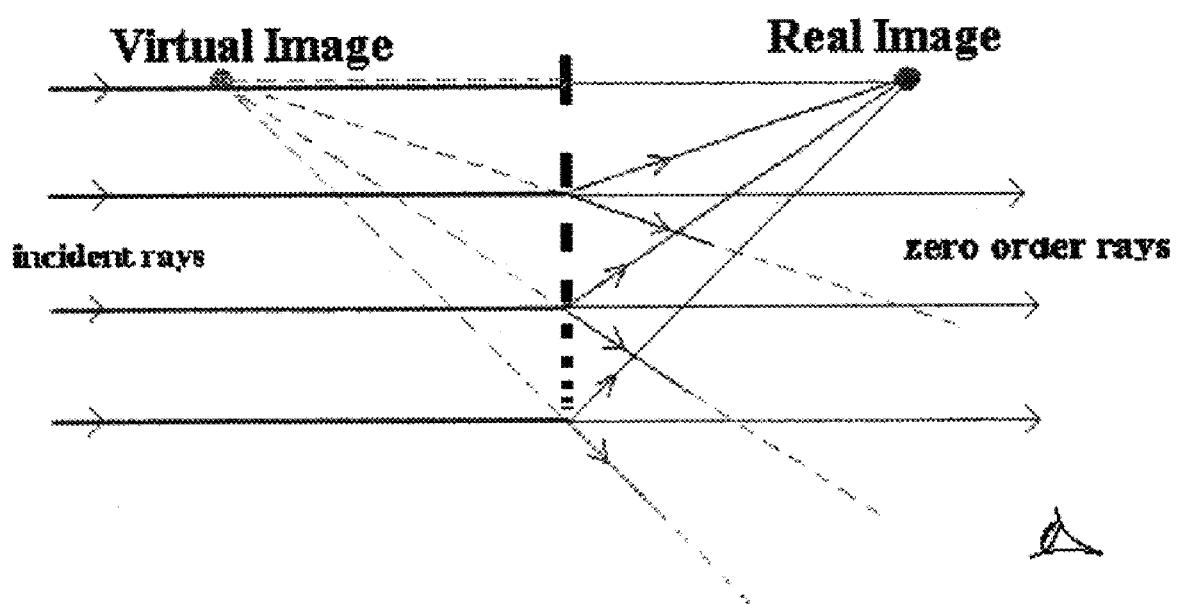
FIG. 19, as described in Example 7, illustrates the twin images arising from the amplitude hologram, the virtual image on the left-hand side of FIG. 19, and the real image on the right-hand side, with the viewer positioned at the lower right-hand corner.

There are two possible objects giving rise to the same hologram pattern due to the uncertainty of pi in recording phase: one is the original object, the other is a virtual object located symmetrically on the other side of the film plane. This concept is illustrated in FIG. 19. FIG. 19 illustrates the twin images arising from the hologram, the virtual image on the left-hand side of FIG. 19, and the real image on the right-hand side, with the viewer positioned at the lower right-hand corner.

Figure 20:
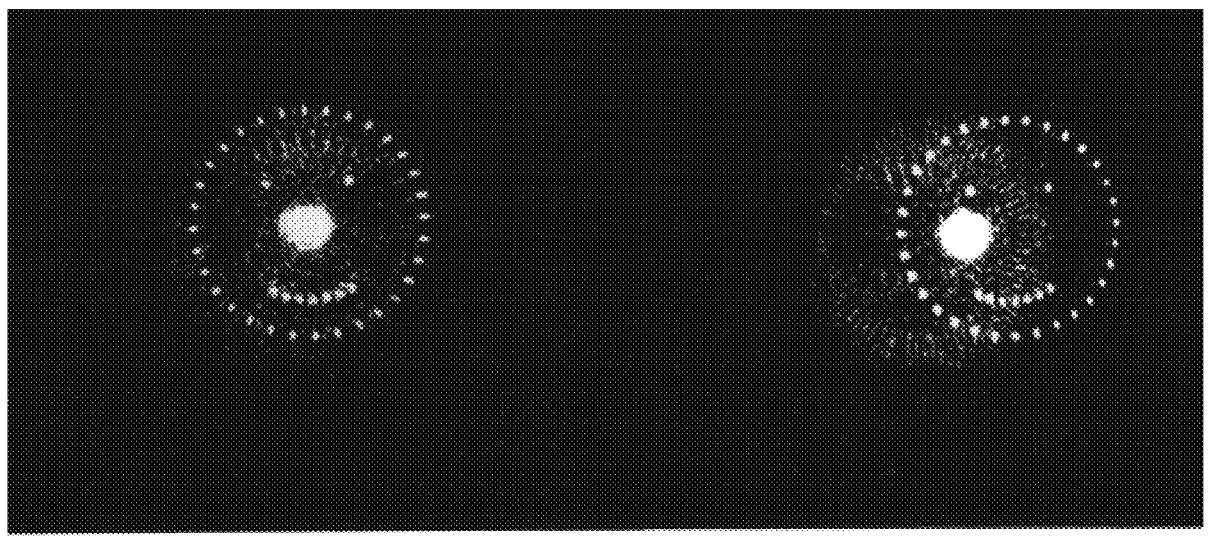
FIG. 20, as described in Example 7, illustrates conjugate beam haze. The in-focus image is the real image, the large dot is the transmitted beam, and the haze is virtual image. The projected image on the left is illuminated through hologram center. Image on right is illuminated slightly off-center to illustrate the symmetric conjugate image placement.

A hologram of a single point consists of symmetric rings on the film plane spaced finer and finer with increased distance from the point center. FIG. 11 is a side-view of the bottom half-plane hologram pattern and it portrays the incident beam, the transmitted beam, and two diffraction orders for each incident ray. The angle of diffraction is set by the local period, just as illustrated in FIG. 11. One set of diffraction orders comprise the real image and converge to a point to the right of the film plane. The other set of orders diverge from the film plane in a pattern that appear to the eye to be coming from a point located at the virtual image. FIG. 20 illustrates conjugate beam haze. The in-focus image is the real image, the large dot is the transmitted beam, and the haze is the virtual image. The projected image on the left is illuminated through hologram center. Image on right is illuminated slightly off-center to illustrate the symmetric conjugate image placement. This figure demonstrates the effect of the twin beam aberration for an example real image. In viewing the image of the real object, one has to look through an out-of-focus background image of the virtual object, a most annoying disturbance, and one of the problems that plagued the first holograms made by Dennis Gabor in 1948. D. Gabor, "A new microscopic principle," *Nature*, vol. 161, pp. 777–778 (1948).

In the early 1960's, Leith and Upatnieks discovered that the twin-beam problem could be alleviated by modulating the signal beam on a carrier to spatially separate the real and virtual image beams. E. N. Leith and J. Upatnieks. "Wavefront reconstruction with diffused illumination and three-dimensional objects." *J. Opt. Soc. Am*, vol. 53, pp. 1377–1381 (1964), incorporated herein by reference. This so-called "off-axis hologram" geometry is accomplished either by centering the object and shifting the reference beam angle, or equivalently, by setting the reference beam to zero and shifting the object off axis. Care must be taken to insure that the combined reference beam angle and the image cone angle are within the limited angular range defined by the sampling period.

Example 8
Fabrication

The challenge one faces in the fabrication process is to faithfully reproduce the hologram features and scale at a reasonable cost. In this Example, an overview is presented of the fabrication steps. The ability to "print" a hologram with responsive material is an important factor in the fabricating a sensing device according to the present invention. The use of MYLAR® as a hologram base substrate is important to high volume, continuous processing, and cost per unit reduction.

The present invention has been developed to enable the positioning of responsive-material in the form of a hologram pattern onto metallized MYLAR®. The steps include: (1) printout of the computer bit map hologram pattern to high-resolution transparency film, (2) photolithoghraphic transfer of the mask pattern to photoresist, (2) formation of an elastomeric stamp from the photoresist relief pattern, (3) thiol monolayer patterning on MYLAR® using the stamp, and (4) responsive gel assembly on the pattern defined by the thiol monolayer.

Example 9

Computer bitmap

Figure 21:
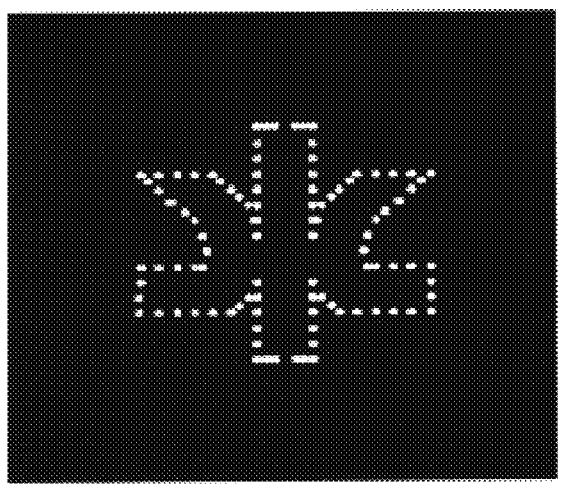
FIG. 21, as described in Example 9, shows a recognizable object on the left-hand side, and its associated hologram on the right-hand side.
Figure 21:
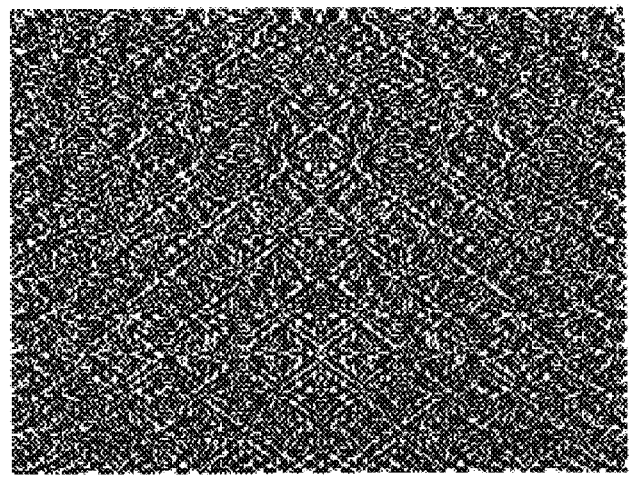

The hologram generated by the computer is initially stored in the form of a 256-level gray-scale bitmap pattern. Each pixel in the bitmap, therefore, is represented by one byte of information. The image storage requirements are set by the total number of samples. For example, a 1000×1000 dot gray-scale bitmap occupies approximately 1 megabyte of memory. An example of the type of hologram pattern that is produced from a recognizable object is shown below in FIG. 21. The recognizable object is on the left-hand side, and its associated hologram is on the right-hand side. The figure on the right is what is patterned. It is a gray-scale representation of the pattern that is produced from the hologram synthesis equation using the image points shown in the figure on the left.

Once the hologram bitmap is calculated, it is converted to a tagged image format (.tif) file and imported into a graphics application such as CorelDraw (Ottawa, Ontario Canada), which is capable of converting the image file to a printer file. Nearly all of the prototype holograms produced for our project were formatted for a 3600 dpi resolution Agfa Selectset 5000 film printer (Ridgefield Park, N.J.).

Figure 22:
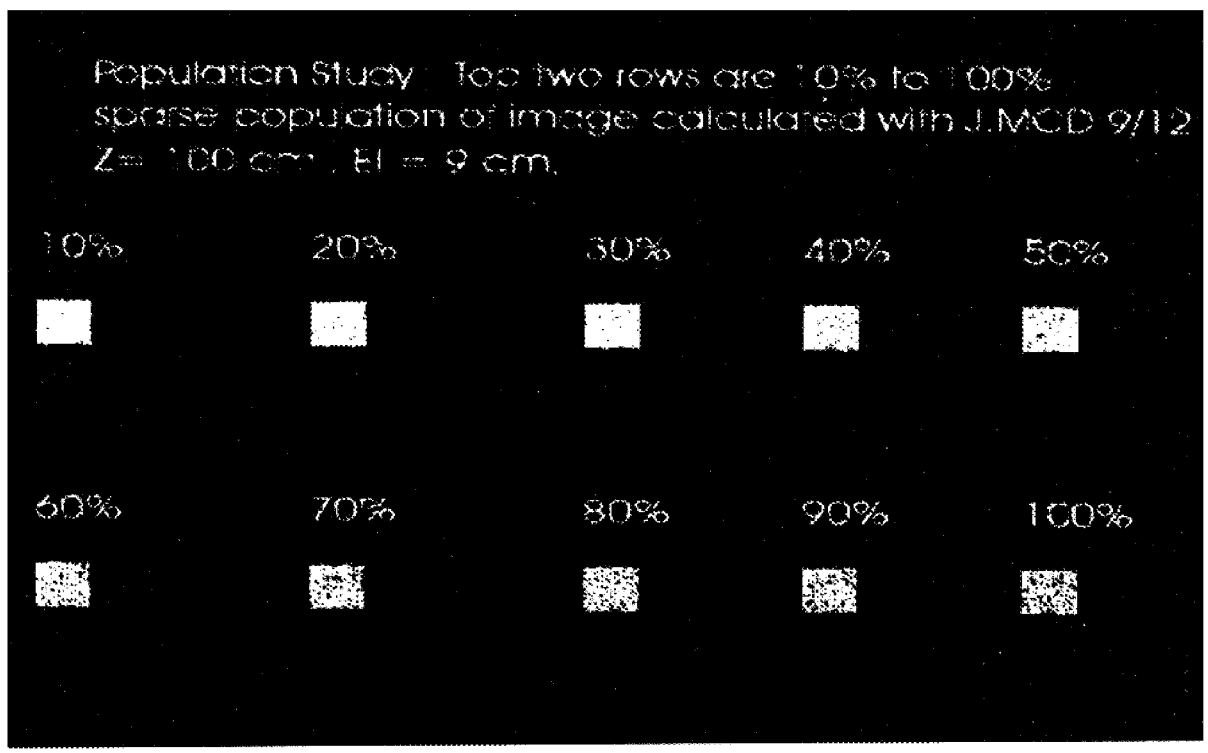
FIG. 22, as described in Example 9, shows a 3600 dots per inch (dpi) test page printout with 20 test holograms on one page.

Several different synthesized holograms can be placed on the same page to minimize the cost per test. FIG. 22 shows a 3600 dots per inch (dpi) test page printout with 20 test holograms on one page. A typical printer file for a multi-test run contains approximately 100 megabytes of information: therefore, a removable "Zip" drive may be utilized to conveniently transfer the file to the service bureau for printout.

The hologram mask is inspected for image quality in both transmission and projection mode before attempting to transfer the pattern to the photoresist-covered substrate. The ability to view the holographic image on the printer-output film saves time in the development process. Images can be evaluated for sampling density, extent limits, and depth before the transfer process is carried out.

Example 10

Photoresist preparation and patterning

The next step in the process is to coat a suitable flat, polished substrate with 1–2 micrometers of photoresist, expose to ultraviolet (UV) light, and develop according to the following procedure):

1. Clean substrate with methanol.
2. Rinse with de-ionized (DI) water.
3. Clean with acetone.
4. Rinse with DI water.
5. Clean with trichloroethane (TCE).
6. Rinse with DI water.
7. Blow off excess with nitrogen stream.
8. Spin to remove any excess water.
9. Bake at 100° C. for 15 minutes to remove water.
10. Pool hexamethyldisilane on wafer and spin at 5000 revolutions per minute (rpm) for 25 seconds.
11. Pool photoresist (Shipley SC1857) on wafer and spin at 5000 for 25 seconds.
12. Bake at 120° C. for 20 minutes. (Don't over bake or photoresist will become brittle).
13. Expose photoresist through mask at approximately 85 mJ/cm$^2$ at 338 nanometers wavelength.
14. Develop with 1:1 (DI water: Shipley concentrate) for 10 seconds to remove exposed photoresist.

The resulting relief-patterned substrate is denoted the "master" and it is the mold from which the elastomeric stamp is formed. An additional step of "de-scumming" the relief wells with a reactive ion etch may be necessary if the bottom of the wells contain any residual photoresist.

Example 11

Elastomeric stamp formation

After the master is fabricated, cleaned, and inspected, it is placed in a vacuum chamber with a small amount of fluorine compound to passivate the surface. Then an elastomer is poured on the master mold and allowed to cure for 16 hours at about 65° C. It is important to coat the surface with the passivation layer first so that the elastomer stamp can peel away from the master when it is set.

Example 12

Final hologram formation

The elastomeric stamp is coated with a hydrophilic thiol and the hologram pattern is printed on a metallized MYLAR® sheet (via the thiol) by carefully pressing the stamp against the MYLAR® and by applying uniform pressure. An analyte-specific responsive gel can then be assembled in the regions defined by the thiol pattern by hydrophilic attraction between the gel and the thiol.

Example 13

Process examples

Figure 23:
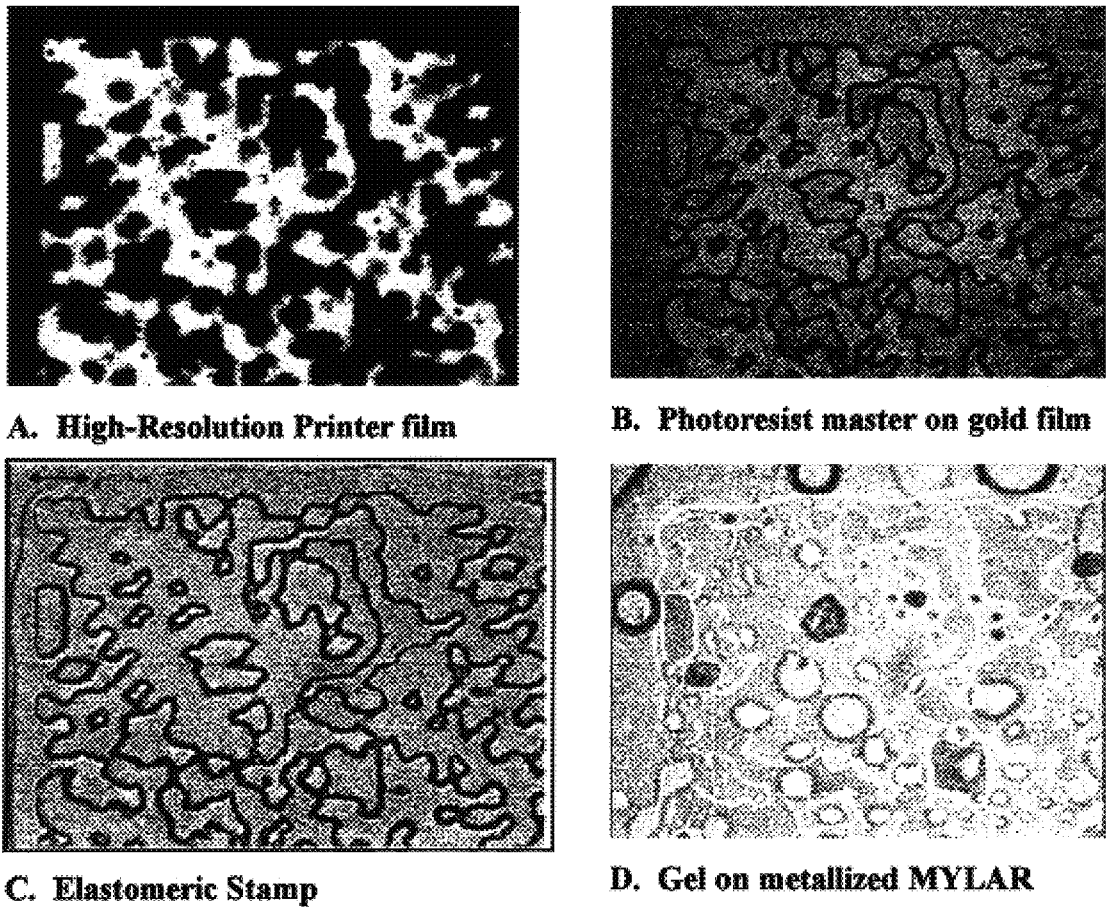
FIG. 23, as described in Example 13, shows several pattern transfer steps from the printer output on high-resolution printer film (A) to the photoresist master on gold film (B) to the elastomer stamp (C) to the responsive gel on metallized Mylar® (D). The small line in (C) is 30 microns long.

There are four transfer steps involved in the hologram production. Each step can be evaluated visually for good pattern replication by microscopy. FIGS. 23 A–D shows several pattern transfer from the printer output on high-resolution printer film (A), to the photoresist master on gold film (B), to the elastomer stamp (C), to the responsive gel on metallized MYLAR®. The small line in (C) is 30 microns long. These figures are corner views of the same pattern at each step. In the FIGS. 23 A–D, the pattern transfer from the printer to the stamp would be judged to be "good" but the quality of the final transfer to the MYLAR® is difficult to judge due to the contrast of the pattern and because of the residual drops of gel which tend to obscure the image.

Figure 9:
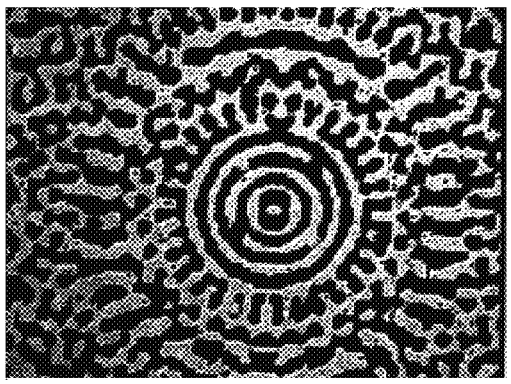
FIG. 9, on the left hand side, shows a hologram diffraction pattern printed on high resolution printer film, as described in Example 13. The right hand side shows a responsive gel atop the same diffraction pattern on metallized Mylar®. The intermediate steps are not shown.
Figure 9:
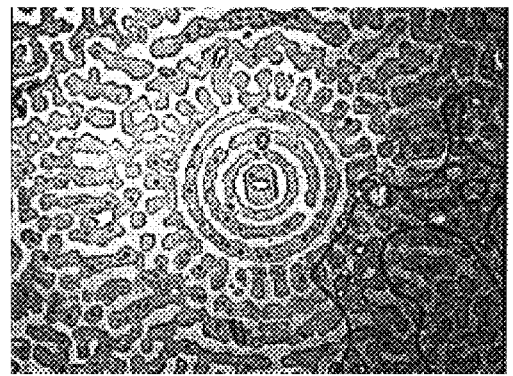

A similar comparison of the hologram's central region, as shown in FIG. 9, indicates a good transfer of the printed pattern to the gel on MYLAR®. The intermediate steps are not shown in this figure.

Example 14

Image Reconstruction

Figure 24:
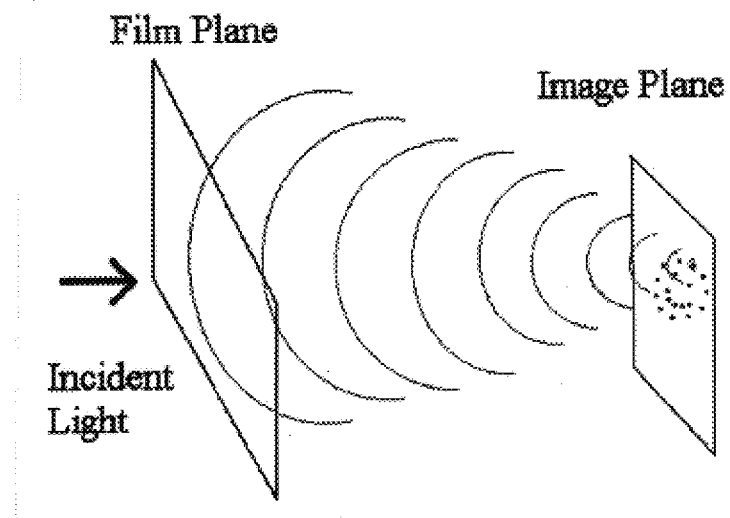
FIG. 24, as described in Example 14, illustrates a method of projecting the real image onto a screen, showing the incident light, the film plane, and the image plane.

The holographic image can be viewed in one of two ways depending on the lighting source. The virtual image can be seen behind the film plane when the hologram is placed between the eye and a white light point source. Alternatively, the real image can be projected on a screen, as shown in FIG. 24, by shining a laser through the hologram. The reconstructed image perspective is determined by the region of beam incidence in the film plane. The fact that each spot in the film contains a separate perspective view of the entire image is one of the most useful characteristics of the hologram, part of the film may become damaged but the image may be viewed simply by moving to a different location on the film.

Another useful attribute associated with the real image reconstruction is shift invariance. Incident light can be scanned across the film plane with no apparent shift in the image. This characteristic is very useful in fixed-position detector systems where precise positioning of the responsive hologram film is impractical.

Figure 7:
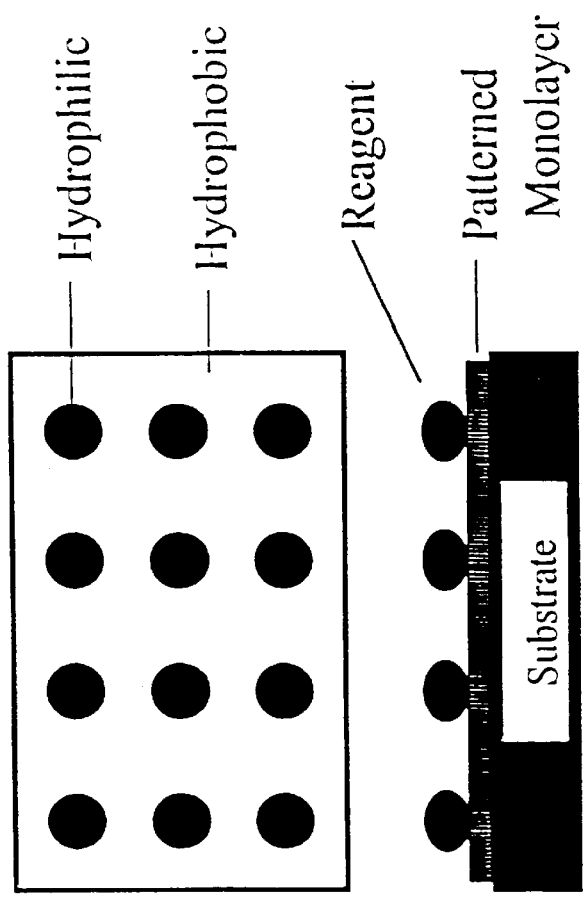
FIG. 7, as described in Example 14, at the left hand side is an illustration of a printed hologram, and the corresponding smiling face image it produces. The right hand side of FIG. 7 are two enlarged views, side plan and top plan, of the circles of self-assembling monolayers which all together make up the printed hologram.
Figure 7:
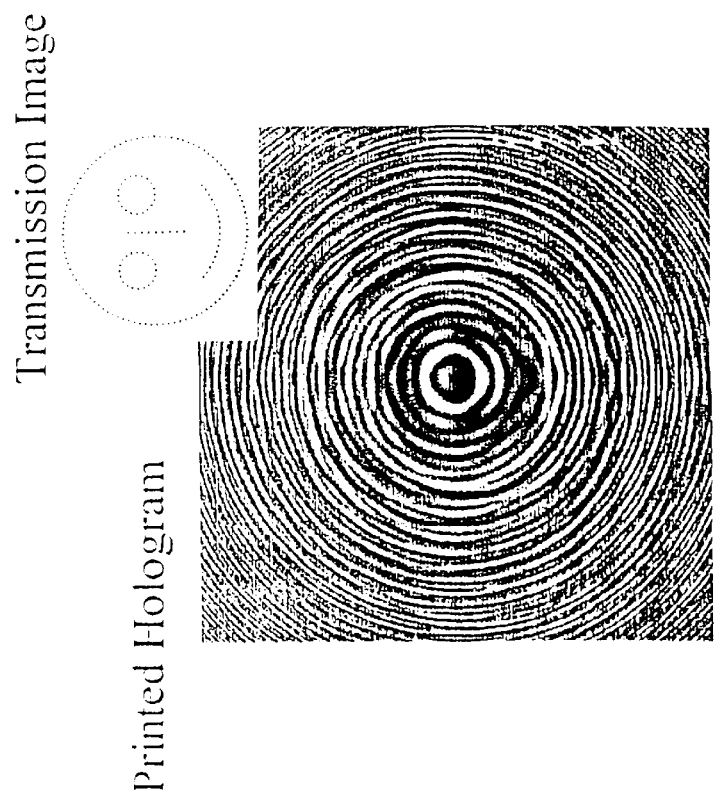

FIG. 7, at the left hand side, is an illustration of a printed hologram, and the corresponding smiling face image it produces The right hand side of FIG. 7 are two enlarged views, side plan and top plan, of the circles of self-assembling monolayers which all together make up the printed hologram.

Example 15

Hologram synthesis algorithm using the MathCad program

The MathCad Program synthesizes the interference patter n required for reconstruction of a 3 dimensional cube made of finite point sources and located behind the film plane. The dimension z is defined in the synthesis equation for each point so that depth can be given to the image.

TOL=$10^{-9}$ mm=$1 \times 10^{-3}$ micrometers=$1 \times 10^{-6}$ cm=$1 \times 10^{-2}$ k=2 pi/$\lambda$ $\lambda$=0.6328 micrometers Fmin 7.056 micrometers Minimum printable feature size, i.e. minimum sample period.

NS=1000 Number of samples in one dimension making up the hologram

EF=FminNS

EF=7.056 mm Maximum extent of hologram window.

Z=6 cm Real image projection (in focus) distance from the film

EI=Ztan[arcsin($\lambda$/Fmin)]

EI=5.403 mm Extent of the projected real image without aliasing xoff=0 Offset of the real image from center requires a modulation.

Theta(R)=arctan(xoff/Z) Required reference beam angle (from film plane normal)

Ef=7. 056 mm

Ei=5.403 mm z=60 mm

Theta(ref)=arctan(sigma(tan(Theta(R))))

N=44 Number of points in the image

Object Point Definitions Defining a Cube $x_o$=(0 2.5 5 7.5 10 10 10 10 10 7.5 5 2.5 0 0 0 0 0 0 0 0 0 0 0000010101010101010)

$y_o$=(000002.557.5 10101010107.552500002.5 5 7.5 10 10 10 10 0 0 0 0 0 2.5 5 7.5)

$z_o$=(0 0 0 00 0 0 0 0 0 0 0 0 0 0 0 2.5 5 7.5 10 10 10 10 10 7.5 5 2.5 2.5 5 7.5 10 10 10 10 1)

$x_0=x_o^T(E_i/20)$ $y_0=y_o^T(E_i/20)$ $z_0=z_o^T(E_i/20)+z$

Film point definitions $\Delta x=E_f/NS$ $\Delta y=\Delta x$ $\Delta x$=7.056 micrometers sampling period i=0 . . . NS-1 j=0 . . . NS-1 $x_i=i\Delta x-E_f/2$ $y_j=j\Delta y-E_f/2$ Interference pattern calculation $$H_{i,j} = \sum \cos\{k[[(x_i - x0_n)^2 + (y_j - y0_n)^2 + (z - z0_n)^2]^{1/2} - [(x0_n)^2 + (y0_n)^2 + (z0_n)^2]^{1/2} - (x_i)\sin(theta(ref))]\}$$

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, all such arrangements, modifications, and alterations are intended to be within the scope of the appended claims. All publications cited herein are incorporated herein by reference.

What is claimed is:

1. A sensing device comprising:
   (a) a self-assembling monolayer stamped in a pattern on a substrate using a stamping means;
   (b) a responsive gel associated with the self-assembling monolayer, the gel capable of responding to a stimulus, wherein the gel is formed from polymers of acrylamides or copolymers containing acrylamides; and
   (c) an additional material on the substrate, the additional material being located on a non-stamped area of the substrate, the additional material being selected such that the responsive gel does not associate with the additional material;
   wherein the self-assembling monolayer is stamped in a pattern such that when the gel responds to the stimulus, the gel undergoes a physical change such that the sensing device produces a change in its diffraction of transmitted electromagnetic radiation, thereby indicating the presence of the stimulus, wherein the change in diffraction is visible to an unaided eye,
   further wherein the physical change occurs discontinuously at a specific stimulus level with a discontinuous change in gel volume.

2. The device of claim 1, wherein the sensing device can form a hologram when electromagnetic radiation is transmitted through the device.

3. The device of claim 2, wherein the hologram changes to a second hologram upon exposure to the stimulus.

4. The device of claim 1, wherein the substrate is selected from the group consisting of glass, silicon dioxide, aluminum oxide, and metallized polymer films.

5. The device of claim 4, wherein the substrate is a polymer film having a metal or metal oxide thereon, and wherein the self-assembling monolayer is formed from compounds with the following general formula:

X—R—Y wherein:
   X is reactive with the metal or metal oxide on the polymer film;
   R is a hydrocarbon chain; and
   Y is a moiety with a surface property of interest.

6. The device of claim 5, wherein:
   X is an asymmetrical or symmetrical disulfide (—R'SSR, —RSSR), sulfide (—R'SR, —RSR), diselinide (—R'SeSeR), selenide (—R'SeR, —RSeR), thiol (—SH), nitrile (—CN), isonitrile, nitro (—NO$_2$), selenol (—SeH), trivalent phosphorous compounds, isothiocyanate, xanthate, thiocarbamate, phosphine, thioacid, dithioacid, carboxylic acids, hydroxylic acids, or hydroxamic acids;

R and R' are hydrocarbon chains which may be interrupted by hetero atoms, and which may be perfluorinated; and Y is a hydroxy, carboxyl, amino, aldehyde, hydrazide, carbonyl, epoxy, or vinyl group.

7. The device of claim 5, wherein R is greater than 7 carbon atoms in length.

8. The device of claim 5, wherein R is a compound of the form $(CH_2)_a$—Z—$(CH_2)_b$, wherein $a \geqq 0$, $b \geqq 7$, and Z is any chemical functionality of interest.

9. The device of claim 8, wherein Z is selected from the group consisting of sulfones, lactams, and urea.

10. The device of claim 4, wherein the substrate is a metallized polymer film, the polymer film comprising polyethylene-terephthalate, acrylonitrile-butadiene-styrene, acrylonitrile-methyl acrylate copolymer, cellophane, cellulosic polymers such as ethyl cellulose, cellulose acetate, cellulose acetate butyrate, cellulose propionate, cellulose triacetate, cellulose triacetate, polyethylene, polyethylene-vinyl acetate copolymers, ionomers (ethylene polymers) polyethylene-nylon copolymers, polypropylene, methyl pentene polymers, polyvinyl fluoride, or aromatic polysulfones.

11. The device of claim 10, wherein the metallized polymer film is optically transparent.

12. The device of claim 10, wherein the metallized polymer film is metallized with metals comprising gold, silver, nickel, platinum, aluminum, iron, copper, zirconium, or alloys thereof.

13. The device of claim 1, wherein the gel is derivatized to contain hydroxyl, carboxyl, amino, aldehyde, carbonyl, epoxy, crown, or vinyl groups.

14. The device of claim 1, wherein the gel contains chromophores, metal salts, ions, antibodies, T or B cell receptors, fragments, or epitopes thereof, proteins, peptides, neurotransmitters, hormones, growth factors, cytokines, monokines, lymphokines, nutrients, enzymes, receptors, macromolecular structures, organelles, cells, or microorganisms.

15. The device of claim 1, wherein the gel contains compounds selected from the group consisting essentially of metallo-phthalocyanines, surfactants, NaBr, KBr, NaCl, KCl, NaI, and KI, methanol and glycerol, tetra-alkylammonium bromides, crown ethers, benzo[18]crown-6, and azobenzene chromophores.

16. The device of claim 1, wherein there are two or more self-assembling monolayers with different physical or chemical properties.

17. The device of claim 1, wherein a first self-assembling monolayer is hydrophobic, and a second self-assembling monolayer is hydrophilic.

18. The device of claim 1, wherein the stimulus comprises temperature, solvent composition, mechanical strain, electric field, pH, salt concentration, solvent quality, light intensity, light wavelength, pressure, ionic strength, ion identity, or specific chemical triggers.

19. A method of making a sensing device comprising stamping a pattern of self-assembling monolayers onto a substrate using a stamping means, applying an additional material to non-stamped areas of the substrate, and coating the pattern of self-assembling monolayers with one or more gels, wherein the gel is associated with the self-assembling monolayers and not associated with the additional material, the gel is formed from polymers of acrylamides or copolymers containing acrylamides, the gels being capable of responding to a stimulus, wherein the self-assembling monolayer is stamped in a pattern such that when the gel responds to the stimulus, the gel undergoes a physical change such that the sensing device produces a change in its diffraction of transmitted electromagnetic radiation, thereby indicating the presence of the stimulus, wherein the change in diffraction is visible to an unaided eye, further wherein the physical change occurs discontinuously at a specific stimulus level with a discontinuous change in gel volume.

20. The method of claim 19, wherein the device can form a hologram when electromagnetic radiation is transmitted through the method.

21. The method of claim 20, wherein, wherein the hologram changes to a second hologram upon exposure to the stimulus.

22. The method of claim 19, wherein the substrate is selected from the group consisting of glass, silicon dioxide, aluminum oxide, and metallized polymer films.

23. The method of claim 22, wherein the substrate is a metallized polymer film, the polymer film comprising polyethylene-terephthalate, acrylonitrile-butadiene-styrene, acrylonitrile-methyl acrylate copolymer, cellophane, cellulosic polymers such as ethyl cellulose, cellulose acetate, cellulose acetate butyrate, cellulose propionate, cellulose triacetate, cellulose triacetate, polyethylene, polyethylene-vinyl acetate copolymers, ionomers (ethylene polymers) polyethylene-nylon copolymers, polypropylene, methyl pentene polymers, polyvinyl fluoride, or aromatic polysulfones.

24. The method of claim 23, wherein the metallized polymer film is optically transparent.

25. The method of claim 23, wherein the metallized polymer film is metallized with metals comprising gold, silver, nickel, platinum, aluminum, iron, copper, zirconium, or alloys thereof.

26. The method of claim 19, wherein the gel is derivatized to contain hydroxyl, carboxyl, amino, aldehyde, carbonyl, epoxy, crown, or vinyl groups.

27. The method of claim 26, wherein the gel contains chromophores, metal salts, ions, antibodies, T or B cell receptors, fragments, or epitopes thereof, proteins, peptides, neurotransmitters, hormones, growth factors, cytokines, monokines, lymphokines, nutrients, enzymes, receptors, macromolecular structures, organelles, cells, or microorganisms.

28. The method of claim 19, wherein the gel contains compounds selected from the group consisting essentially of metallo-phthalocyanines, surfactants, NaBr, KBr, NaCl, KCl, NaI, and KI, methanol and glycerol, tetra-alkylammonium bromides, crown ethers, benzo[18]crown-6, azobenzene chromophores.

29. The method of claim 19, wherein there are two or more self-assembling monolayers with different physical or chemical properties.

30. The method of claim 19, wherein a first self-assembling monolayer is hydrophobic, and a second self-assembling monolayer is hydrophilic.

31. The method of claim 19, wherein the substrate is a polymer film having a metal or metal oxide thereon, and wherein the self-assembling monolayer is formed from compounds with the following general formula:

wherein:
    X is reactive with the metal or metal oxide on the polymer film;

R is a hydrocarbon chain; and

Y is a moiety with a surface property of interest.

32. The method of claim 31, wherein:

X is an asymmetrical or symmetrical disulfide (—R'SSR, —RSSR), sulfide (—R'SR, —RSR), diselinide (—R'SeSeR), selenide (—R'SeR, —RSeR), thiol (—SH), nitrile (—CN), isonitrile, nitro (—NO$_2$), selenol (—SeH), trivalent phosphorous compounds, isothiocyanate, xanthate, thiocarbamate, phosphine, thioacid, dithioacid, carboxylic acids, hydroxylic acids, or hydroxamic acids;

R and R' are hydrocarbon chains which may be interrupted by hetero atoms, and which may be perfluorinated; and Y is a hydroxy, carboxyl, amino, aldehyde, hydrazide, carbonyl, epoxy, or vinyl group.

33. The method of claim 31, wherein R is greater than 7 carbon atoms in length.

34. The method of claim 31, wherein R is a compound of the form $(CH_2)_a$—Z—$(CH_2)_b$, wherein $a \geq 0$, $b \geq 7$, and Z is any chemical functionality of interest.

35. The method of claim 34, wherein Z is selected from the group consisting of sulfones, lactams, and urea.

36. The method of claim 19, wherein the stimulus comprises temperature, solvent composition, mechanical strain, electric field, pH, salt concentration, solvent quality, light intensity, light wavelength, pressure, ionic strength, ion identity, or specific chemical triggers.

* * * * *